United States Patent [19]

Gallatin et al.

[11] Patent Number: 5,532,127
[45] Date of Patent: Jul. 2, 1996

[54] ASSAY FOR 1-CAM RELATED PROTEIN EXPRESSION

[75] Inventors: W. Michael Gallatin; Rosemay Vazeux, both of Seattle, Wash.

[73] Assignee: ICOS Corporation, Bothell, Wash.

[21] Appl. No.: 314,362

[22] Filed: Sep. 28, 1994

Related U.S. Application Data

[63] Continuation of Ser. No. 894,061, Jun. 5, 1992, abandoned, which is a continuation-in-part of Ser. No. 889,724, May 26, 1992, abandoned, which is a continuation-in-part of Ser. No. 827,689, Jan. 27, 1992, abandoned.

[51] Int. Cl.$^6$ .......................... C12Q 1/68; C07K 14/725; C07H 17/00
[52] U.S. Cl. .................. 435/6; 935/78; 530/350; 536/23.1; 536/24.32
[58] Field of Search .................. 435/69.1, 69.3, 435/6; 530/350; 536/23.1, 24.32; 935/78

[56] References Cited

U.S. PATENT DOCUMENTS

5,081,034  1/1991  Bevilacqua et al. ............... 435/252.33

FOREIGN PATENT DOCUMENTS

| | | |
|---|---|---|
| 289949 | 11/1988 | European Pat. Off. . |
| 314863 | 5/1989 | European Pat. Off. . |
| 314317 | 5/1989 | European Pat. Off. . |
| 362531 | 4/1990 | European Pat. Off. . |
| 387668 | 9/1990 | European Pat. Off. . |
| 386906 | 9/1990 | European Pat. Off. . |
| 408859 | 1/1991 | European Pat. Off. . |
| 468257 | 1/1992 | European Pat. Off. . |
| WO88/06592 | 9/1988 | WIPO . |
| WO89/02922 | 4/1989 | WIPO . |
| WO90/05786 | 5/1990 | WIPO . |
| WO90/05539 | 5/1990 | WIPO . |
| WO90/06953 | 6/1990 | WIPO . |
| WO90/13300 | 11/1990 | WIPO . |
| WO91/10683 | 7/1991 | WIPO . |
| WO91/18011 | 11/1991 | WIPO . |
| WO91/16928 | 11/1991 | WIPO . |
| WO91/18010 | 11/1991 | WIPO . |
| WO92/00751 | 1/1992 | WIPO . |
| WO92/04034 | 3/1992 | WIPO . |
| WO92/06119 | 4/1992 | WIPO . |
| WO92/22323 | 12/1992 | WIPO . |

OTHER PUBLICATIONS

Sambrook et al. 1989 Molecular Cloning: A Laboratory Manual Cold Spring Harbor Laboratory, CSH, N.Y.
Seid et al. 1987 PNAS 84: 3365–3369.
Hadam, "N11 Cluster Report: CDw50", pp. 667–670 in Knapp et al., eds., Leukocyte Typing IV, Oxford, Oxford University Press (1989).
Juan et al., "CDw50 and ICAM–3: Two names for the same molecule", Eur. J. Immunol., 23: 1508–1512 (1993).
Knapp et al., "CD Antigens 1989", Blood, 74(4): 1448–1450 (Sep. 1989).
Lozano et al., "Effect of protein kinase C activators on the phosphorylation and the surface expression of the CDw50 leukocyte antigen", Eur. J. Biochem., 203: 321–326 (Mar. 1992).
Lozano et al., "Isolation and Characterisation of a CDw50 Negative Jurkat T–Cell Line Variant", Leukemia Research, 17(1): 9–16 (1993).
Vilella et al., "Involvement of the CDw50 molecule in allorecognition", Tissue Antigens, 36: 203–210 (1990).
DeFougerolles et al., "Cloning and Expression of Intercellular Adhesion Molecule 3 Reveals Strong Homology to Other Immunoglobulin Family Counter–receptors for Lymphocyte Function–associated Antigen 1", J. Exp. Med., 177: 1187–1192 (Apr. 1993).
Ashkenazi et al., Proc. Natl. Acad. Sci. USA, 88: 10535–10539 (1991).
Capon et al., Nature, 337: 525–531 (1989).
Chen et al., Molecular and Cellular Biology, 7: 2745–2748 (1987).
Corpet et al., Nucleic Acids Res., 16(22): 10881–10890 (1988).
de Fougerolles et al., J. Exp. Med., 174: 253–267 (1991).
de Fougerolles et al., J. Exp. Med., 175: 185–190 (1992).
Edwards, Current Opinion in Therapeutic Patents, 1(11): 1617–1630 (1991).
Fawcett et al., Nature, 360: 481–484 (1992).
Hunkapiller et al., Nature, 323: 15–16 (1986).
Newman et al., Science, 247: 1219–1222 (1990).
Springer, Nature, 346: 425–434 (1990).
Vazeux et al., Nature, 360: 485–488 (1992).
Williams et al., Ann. Rev. Immunol., 6: 381–405 (1988).

Primary Examiner—Robert A. Wax
Assistant Examiner—K. Cochrane Carlson
Attorney, Agent, or Firm—Marshall, O'Toole, Gerstein, Murray & Borun

[57] ABSTRACT

DNA sequences encoding a novel human intercellular adhesion molecule polypeptide (designated "ICAM-R") and variants thereof are disclosed along with methods and materials for production of the same by recombinant procedures. Antibodies substances specific for ICAM-R and variants thereof are also disclosed as useful in both the isolation of ICAM-R from natural cellular sources and the modulation of ligand/receptor binding reactions involving ICAM-R.

1 Claim, 25 Drawing Sheets

```
CAGCTCTCTGTCAGA ATG GCC ACC ATG GTA CCA TCC GTG TTG TGG CCC                          48
                 M   A   T   M   V   P   S   V   L   W   P
                -29             -26 -25                 -20

AGG GCC TGG ACT CTG CTG GTC TGC TGT CTG CTG ACC CCA GGT                              93
 R   A   W   T   L   L   V   C   C   L   L   T   P   G
            -15                         -10                 -5

GTC CAG GGG CAG GAG TTC CTT TTG CGG GTG GAG CCC CAG AAC CCT                         138
 V   Q   G   Q   E   F   L   L   R   V   E   P   Q   N   P
        -1  +1              5                       10

GTG CTC TCT GCT GGA GGG TCC CTG TTT GTG AAC TGC AGT ACT GAT                         183
 V   L   S   A   G   G   S   L   F   V   N*  C   S   T   D
                15                  20                  25

TGT CCC AGC TCT GAG AAA ATC GCC TTG GAG ACG TCC CTA TCA AAG                         228
 C   P   S   S   E   K   I   A   L   E   T   S   L   S   K
                30                  35                  40

GAG CTG GTG GCC AGT GGC ATG GGC TGG GCA GCC TTC AAT CTC AGC                         273
 E   L   V   A   S   G   M   G   W   A   A   F   N*  L   S
                45                  50                  55
```

FIGURE 1A

```
AAC GTG ACT GGC AAC AGT CGG ATC CTC TGC TCA GTG TAC TGC AAT      318
 N*  V   T   G   N   S   R   I   L   C   S   V   Y   C   N*
            60                  65                  70

GGC TCC CAG ATA ACA GGC TCC TCT AAC ATC ACC GTG TAC GGG CTC      363
 G   S   Q   I   T   G   S   S   N*  I   T   V   Y   G   L
            75                  80                  85

CCG GAG CGT GTG GAG CTG GCA CCC CTG CCT CCT TGG CAG CCG GTG      408
 P   E   R   V   E   L   A   P   L   P   P   W   Q   P   V
            90                  95                  100

GGC CAG AAC TTC ACC CTG CGC TGC CAA GTG GAG GGT TCG CCC          453
 G   Q   N*  F   T   L   R   C   Q   V   E   G   S   P
            105                 110                 115

CGG ACC AGC CTC ACG GTG GTG CTG CTT CGC TGG GAG GAG CTG          498
 R   T   S   L   T   V   V   L   L   R   W   E   E   L
            120                 125                 130

AGC CGG CAG CCC GCA GTG GAG GAG CCA GCG GAG GTC ACT GCC ACT      543
 S   R   Q   P   A   V   E   E   P   A   E   V   T   A   T
            135                 140                 145
```

FIGURE 1B

| | | | | | | | | | | | | | | | |
|---|---|---|---|---|---|---|---|---|---|---|---|---|---|---|---|
| GTG | CTG | GCC | AGC | AGA | GAC | GAC | CAC | GGA | GCC | CCT | TTC | TCA | TGC | CGC | 588 |
| V | L | A | S | R | D | D | H | G | A | P | F | S | C | R | |
| | | 150 | | | | 155 | | | | 160 | | | | | |

| | | | | | | | | | | | | | | | |
|---|---|---|---|---|---|---|---|---|---|---|---|---|---|---|---|
| ACA | GAA | CTG | GAC | ATG | CAG | CCC | CAG | GGG | CTG | GGA | CTG | TTC | GTG | AAC | 633 |
| T | E | L | D | M | Q | P | Q | G | L | G | L | F | V | N* | |
| | | 165 | | | | 170 | | | | 175 | | | | | |

| | | | | | | | | | | | | | | | |
|---|---|---|---|---|---|---|---|---|---|---|---|---|---|---|---|
| ACC | TCA | GCC | CCC | CGC | CAG | CTC | CGA | ACC | TTT | GTC | CTG | CCC | GTG | ACC | 678 |
| T | S | A | P | R | Q | L | R | T | F | V | L | P | V | T | |
| | | 180 | | | | 185 | | | | 190 | | | | | |

| | | | | | | | | | | | | | | | |
|---|---|---|---|---|---|---|---|---|---|---|---|---|---|---|---|
| CCC | CCG | CGC | CTC | GTG | GCC | CCC | CGG | TTC | CTC | TTG | GAG | GTG | GAA | ACG | TCG | 723 |
| P | P | R | L | V | A | P | R | F | L | L | E | V | E | T | S |
| | | 195 | | | | 200 | | | | 205 | | | | | |

| | | | | | | | | | | | | | | | |
|---|---|---|---|---|---|---|---|---|---|---|---|---|---|---|---|
| TGG | CCG | GTG | GAC | TGC | ACC | CTA | GAC | GGG | CTT | TTT | CCA | GCC | TCA | GAG | 768 |
| W | P | V | D | C | T | L | D | G | L | F | P | A | S | E | |
| | | 210 | | | | 215 | | | | 220 | | | | | |

| | | | | | | | | | | | | | | | |
|---|---|---|---|---|---|---|---|---|---|---|---|---|---|---|---|
| GCC | CAG | GTC | TAC | CTG | GCG | CTG | GGG | GAC | CAG | ATG | CTG | AAT | GCG | ACA | 813 |
| A | Q | V | Y | L | A | L | G | D | Q | M | L | N* | A | T | |
| | | 225 | | | | 230 | | | | 235 | | | | | |

FIGURE 1C

```
GTC ATG AAC CAC GGG GAC ACG CTA ACG GCC ACA GCC ACG        858
 V   M   N   H   G   D   T   L   T   A   T   A   T
                         245                 250

GCG CGC GCG GAT CAG GAG GGT GCC CGG GAG ATC GTC TGC AAC GTG  903
 A   R   A   D   Q   E   G   A   R   E   I   V   C   N*  V
                 255                 260                 265

ACC CTA GGG GGC GAG AGA CGG GAG GCC CGG GAG AAC TTG ACG GTC  948
 T   L   G   G   E   R   R   E   A   R   E   N*  L   T   V
                 270                 275                 280

TTT AGC TTC CTA GGA CCC ATT GTG AAC CTC AGC GAG CCC ACC GCC  993
 F   S   F   L   G   P   I   V   N*  L   S   E   P   T   A
             285                 290                 295

CAT GAG GGG TCC ACA GTG ACC GTG AGT TGC ATG GCT GGG GCT CGA 1038
 H   E   G   S   T   V   T   V   S   C   M   A   G   A   R
             300                 305                 310

GTC CAG GTC ACG CTG GAC GGA GTT CCG GCC GCG GCC CCG GGG CAG 1083
 V   Q   V   T   L   D   G   V   P   A   A   A   P   G   Q
             315                 320                 325
```

FIGURE 1D

```
CCA GCT CAA CTT CAG CTA AAT GCT ACC GAG AGT GAC GAC GGA CGC    1128
 P   A   Q   L   Q   L   N*  A   T   E   S   D   D   G   R
                     330                 335                 340

AGC TTC TTC TGC AGT GCC ACT CTC GAG GTG GAC GGC GAG TTC TTG    1173
 S   F   F   C   S   A   T   L   E   V   D   G   E   F   L
                     345                 350                 355

CAC AGG AAC AGT AGC GTC CAG CTG CGA GTC CTG TAT GGT CCC AAA    1218
 H   R   N*  S   S   V   Q   L   R   V   L   Y   G   P   K
                     360                 365                 370

ATT GAC CGA GCC ACA TGC CCC CAG CAC TTG AAA TGG AAA GAT AAA    1263
 I   D   R   A   T   C   P   Q   H   L   K   W   K   D   K
             375                 380                 385

ACG AGA CAC GTC CTG CAG TGC CAA GCC AGG GGC AAC CCG TAC CCC    1308
 T   R   H   V   L   Q   C   Q   A   R   G   N   P   Y   P
             390                 395                 400

GAG CTG CGG TGT TTG AAG GAA GGC TCC AGC CGG GAG GTG CCG GTG    1353
 E   L   R   C   L   K   E   G   S   S   R   E   V   P   V
         405                 410                 415
```

FIGURE 1E

```
GGG ATC CCG TTC TTC GTC AAC GTA ACA CAT AAT GGT ACT TAT CAG      1398
 G   I   P   F   F   V   N*  V   T   H   N*  G   T   Y   Q
                420             425             430

TGC CAA GCG TCC AGC TCA CGA GGC AAA TAC ACC CTG GTC GTG GTG      1443
 C   Q   A   S   S   S   R   G   K   Y   T   L   V   V   V
                435             440             445

ATG GAC ATT GAG GCT GGG AGC TCC CAC TTT GTC CCC GTC TTC GTG      1488
 M   D   I   E   A   G   S   S   H   F---V---P---V---F---V---
                450             455             460

GCG GTG TTA CTG ACC CTG GGC GTG ACT ATC GTA CTG GCC TTA          1533
 A---V---L---L---T---L---G---V---T---I---V---L---A---L---
                465             470             475

ATG TAC GTC TTC AGG GAG CAC CAA CGG AGC GGC AGT TAC CAT GTT      1578
 M---Y---V---F---R   E   H   Q   R   S   G   S   Y   H   V
                480             485             490

AGG GAG GAG AGC ACC TAT CTG CCC CTC ACG TCT ATG CAG CCG ACA      1623
 R   E   E   S   T   Y   L   P   L   T   S   M   Q   P   T
                495             500             505
```

FIGURE 1F

```
GAA GCA ATG GGG GAA GAA CCG TCC AGA GCT GAG TGACGCTGGGATCCG      1671
 E   A   M   G   E   E   P   S   R   A   E
            510             515             518

GGATCAAAGTTGGGCGGGGGGCTTGGCTGTGCCCTCAGATTCCGCACCAATAAAGCCTTCA   1730

AACTCCCAAAAAAAAAAAAAAAAAAAAAAAAAAAAAAAAAAAAAAAAAAA              1781
```

ASSAY FOR 1-CAM RELATED PROTEIN EXPRESSION

This is a Rule 62 file wrapper continuation of U.S. patent application Ser. No. 07/894,061, filed Jun. 5, 1992, now abandoned, which is a continuation-in-part of U.S. Pat. Application Ser. No. 07/889,724, filed May 26, 1992, now abandoned which is in turn a continuation-in-part of U.S. patent application Ser. No. 07/827,689, filed Jan 27, 1992, now abandoned.

BACKGROUND OF THE INVENTION

The present invention relates generally to cellular adhesion molecules and more particularly to the cloning and expression of DNA encoding a heretofore unknown human polypeptide designated "ICAM-R" which possesses structural relatedness to the human intercellular adhesion molecules ICAM-1 and ICAM-2.

Research spanning the last decade has significantly elucidated the molecular events attending cell-cell interactions in the body, especially those events involved in the movement and activation of cells in the immune system. See generally, Springer, *Nature,* 346:425–434 (1990). Cell surface proteins, and especially the so-called Cellular Adhesion Molecules ("CAMs") have correspondingly been the subject of pharmaceutical research and development having as its goal intervening in the processes of leukocyte extravasation to sites of inflammation and leukocyte movement to distinct target tissues. The isolation and characterization of cellular adhesion molecules, the cloning and expression of DNA sequences encoding such molecules, and the development of therapeutic and diagnostic agents relevant to inflammatory processes, viral infection and cancer metastasis have also been the subject of numerous U.S. and foreign applications for Letters Patent. See Edwards, *Current Opinion in Therapeutic Patents,* 1(11):1617–1630 (1991) and particularly the published "patent literature references" cited therein.

Of fundamental interest to the background of the present invention is the prior identification and characterization of certain mediators of cell adhesion events, the "leukointegrins," LFA-1, MAC-1 and gp 150.95 (referred to in WHO nomenclature as CD 18/CD 11a, CD 18/CD 11b, and CD 18/CD 11c, respectively) which form a subfamily of heterodimeric "integrin" cell surface proteins present on B lymphocytes, T lymphocytes monocytes and granulocytes. See, e.g., Table 1 of Springer, supra, at page 429. Also of interest are other single chain adhesion molecules (CAMs) which have been implicated in leukocyte activation, adhesion, motility and the like, events attendant the inflammatory process. For example, it is presently believed that prior to the leukocyte extravasation which characterizes inflammatory processes, activation of integrins constitutively expressed on leukocytes occurs and there follows a tight ligand/receptor interaction between the integrins (e.g., LFA-1) and one or both distinct intercellular adhesion molecules (ICAMs) designated ICAM- 1 and ICAM-2, which are expressed on blood vessel endothelial cell surfaces and on other leukocytes.

Like the other CAMs characterized to date, [e.g., vascular adhesion molecule (VCAM-1) as described in PCT WO 90/13300 published Nov 15, 1990; and platelet endothelial cell adhesion molecule (PECAM-1)as described in Newman et al. *Science* 247:1219–1222 (1990) and PCT WO 91/10683 published Jul. 25, 1991], ICAM-1 and ICAM-2 share structural homology with other members of the immunoglobulin gene superfamily in that each is comprised of a series of domains sharing a similar motif near their ends. An individual domain typically contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A variety of therapeutic uses have been projected for intercellular adhesion molecules, including uses premised on the ability of ICAM-1 to bind human rhinovirus. European Patent Application 468 257 A published Jan 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as plasmodium falciparum.

In a like manner, a variety of uses have been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxin shock in WO92/04034, published Mar 19, 1992. Inhibition of ICAM-1 dependent inflammatory responses with anti-ICAM-1 anti-idiotypic antibodies and fragments thereof is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. Quite recently, for example, Springer and his co-workers postulated the existence of a third counter-receptor for LFA-1 [de Fougerolles, et al., *J. Exp. Med.,* 174:253–267 (1991)] and subsequently reported success in immunoprecipitating a "third" ICAM ligand, designated "ICAM-3" [de Fougerolles, et al., *J. Exp. Med.,* 175:185–190 (1992)]. This molecule was reported to bind soluble LFA-1 and to be highly expressed by resting lymphocytes, monocytes and neutrophils. Unlike ICAM-1 and ICAM-2, however, the new ligand was not found to be expressed by endothelial cells. The immunoprecipitated product was noted to display a molecular weight of about 124,000 and to be heavily glycosylated, as revealed by a drop in apparent molecular weight to about 87,000 upon N-glyanase treatment.

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY

In one of its aspects, the present invention provides purified and isolated polynucleotides (e.g., DNA sequences and RNA transcripts thereof) encoding a novel human polypeptide, "ICAM-R," as well as polypeptide variants (including fragments and analogs) thereof which display one or more ligand/receptor binding biological activities and/or immunological properties specific to ICAM-R. Preferred DNA sequences of the invention include genomic and cDNA sequences as well as wholly or partially chemically synthesized DNA sequences and biological replicas thereof. Also provided are autonomously replicating recombinant constructions such as plasmid and viral DNA vectors incorporating such sequences and especially vectors wherein DNA encoding ICAM-R or an ICAM-R variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-R and ICAM-R variant products can serve a variety of useful purposes. To the extent that the expressed products are "displayed" on host cell surfaces, the cells may constitute a valuable immunogen for the development of antibody substances specifically immunoreactive with ICAM-R and ICAM-R variants. Host cells of the invention are conspicuously useful in methods for the large scale production of ICAM-R and ICAM-R variants wherein the cells are grown in a suitable culture medium and the desired polypeptide products are isolated from the cells or from the medium in which the cells are grown.

Novel ICAM-R and ICAM-R variant products of the invention may be obtained as isolates from natural cell sources, but are preferably produced by recombinant procedures involving host cells of the invention. The products may be obtained in fully or partially glycosylated, partially or wholly de-glycosylated, or non-glycosylated forms, depending on the host cell selected for recombinant production and/or post-isolation processing.

Products of the invention include monomeric and multimeric polypeptides having the sequence of amino acid residues numbered −29 through 518 as set out in SEQ ID NO: 1 herein. As explained in detail infra, this sequence includes a putative signal or leader sequence which precedes the "mature" protein sequence and spans residues −29 through −1, followed by the putative mature protein including, in order, five putative immunoglobulin-like domains (respectively spanning residues 1 to 90, 91 to 187, 188 to 285, 286 to 387, and 388 to about 456), a hydrophobic "transmembrane" region extending from about residue 457 to about residue 481 and a "cytoplasmic" region constituting the balance of the polypeptide at its carboxy terminus. Based on amino acid composition, the calculated molecular weight of the mature protein lacking glycosylation or other post-translational modification is approximately 52,417. ICAM-R variants of the invention may comprise water soluble and insoluble ICAM-R fragments including one or more of the regions specified above and may also comprise polypeptide analogs wherein one or more of the specified amino acids is deleted or replaced: (1) without loss, and preferably with enhancement, of one or more biological activities or immunological characteristics specific for ICAM-R; or (2) with specific disablement of a particular ligand/receptor binding function. Analog polypeptides including additional amino acid (e.g., lysine) residues that facilitate multimer formation are contemplated.

Also comprehended by the present invention are antibody substances (e.g., monoclonal and polyclonal antibodies, single chain antibodies, chimeric antibodies, CDR-grafted antibodies and the like) or other binding proteins which are specific for ICAM-R or ICAM-R variants (i.e., non-reactive with the ICAM-1 and ICAM-2 intercellular adhesion molecules to which ICAM-R is structurally related). Antibody substances can be developed using isolated natural or recombinant ICAM-R or ICAM-R variants or cells expressing such products on their surfaces. Specifically illustrating antibody substances according to the present invention are the monoclonal antibodies produced by the four hybridoma cells lines designated 26I10E-2, 26E3D-1, 26H11C-2 and 26I8F-2, which were respectively deposited with the American Type Culture Collection on Jun. 2, 1992 as Accession Nos. HB 11053, HB 11054, HB 11055 and HB 11056.

The antibody substances are useful, in turn, for use in complexes for immunization as well as for purifying polypeptides of the invention and identifying cells producing the polypeptides on their surfaces. The antibody substances are also manifestly useful in modulating (i.e., blocking, inhibiting or stimulating) ligand/receptor binding reactions involving ICAM-R, especially those involved in inflammation resulting from specific and non-specific immune system responses. Anti-idiotypic antibodies specific for anti-ICAM-R antibody substances and uses of such anti-idiotypic antibody substances in treatment of inflammation are also contemplated. Assays for the detection and quantification of ICAM-R on cell surfaces and in fluids such as serum may involve a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for ICAM-R makes possible the isolation by DNA/DNA hybridization of genomic DNA sequences encoding ICAM-R and specifying ICAM-R expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-R, other structurally related proteins sharing the biological and/or immunological specificity of ICAM-R, and non-human species proteins homologous to ICAM-R. DNAs of the invention are useful in DNA/RNA hybridization assays to detect the capacity of cells to synthesize ICAM-R. Also made available by the invention are anti-sense polynucleotides relevant to regulating expression of ICAM-R by those cells which ordinarily express the same. As another series of examples, knowledge of the DNA and amino acid sequences of ICAM-R make possible the generation by recombinant means of hybrid fusion proteins (sometimes referred to as "immunoadhesins") characterized by the presence of ICAM-R protein sequences and immunoglobulin heavy chain constant regions and/or hinge regions. See, Capon, et al., *Nature*, 337:525–531 (1989); Ashkenazi, et al., *P.N.A.S. (USA)*, 88:10535–10539 (1991); and PCT WO 89/02922, published Apr. 6, 1989.

Numerous other aspects and advantages of the present invention will therefore be apparent upon consideration of the following detailed description thereof, reference being made to the drawing wherein:

FIG. 1(A through G) depicts an isolated cDNA clone insert (SEQ ID NO: 2) derived from HL60 cells encoding ICAM-R and the deduced amino acid sequence (SEQ ID NO: 1) of an open reading frame therein;

FIG. 2(A through B) comprises bar graphs illustrating the results of northern blot hybridization of transfected L cells using ICAM-R and ICAM-1 DNA probes;

FIG. 3(A through F) presents photomicrographs depicting the results of in situ hybridizations of transfected L cells using ICAM-R or ICAM-1 RNA probes;

FIG. 4 illustrates in histogram format the results of FACS analyses of indirect immunofluorenscence staining of transfected L cells using monoclonal antibodies specific for ICAM-R, ICAM-1 or ICAM-2.

FIG. 5(A through B) presents bar graphs depicting the results of actin-normalized northern blot hybridization of human leukocyte cell lines and umbilical cord endothelial cells using ICAM-R or ICAM-1 DNA probes;

FIG. 6(A through B) are photographs of western blots of immunoprecipitations of lysates from human cells lines using ICAM-R specific monoclonal antibodies; and FIG. 7(A through G) presents photomicrographs of immunohistologic staining of various human tissues with an anti-ICAM-R monoclonal antibody.

DETAILED DESCRIPTION

Figure 2A:
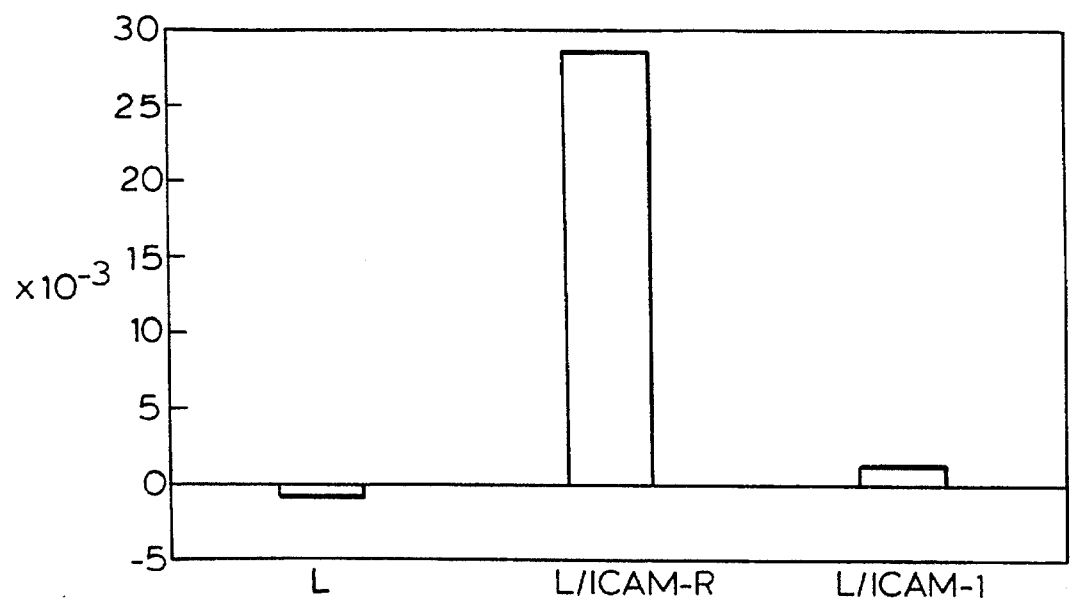

The present invention is illustrated by the following examples relating to the isolation of a full length cDNA clone encoding ICAM-R from a cDNA library derived from human HL60 promyelocytic cells (ATCC CCL 240) and to the expression of ICAM-R DNA in L cells. More particularly, Example 1 addresses the design and construction of oligonucleotide probes for PCR amplification of ICAM related DNAs. Example 2 addresses the use of the probes to amplify a genomic DNA fragment homologous to, but distinct from, DNAs encoding ICAM-1 and ICAM-2. Example 3 treats the screening of cDNA libraries with the genomic fragment to isolate additional ICAM-R coding sequences. Example 4 refers to the further screening of cDNA libraries to isolate a full length cDNA encoding ICAM-R. Example 5 provides a characterization of DNA and amino acid sequence information for ICAM-R and relates the structures thereof to ICAM-1 and ICAM-2. Example 6 describes the development of host cells expressing ICAM-R. Example 7 relates to the preparation of anti-ICAM-R antibodies. Examples 8, 9 and 10 relate to assessment of the distribution of ICAM-R polypeptide and RNA encoding the same in normal cells and tissues as well as in various cell lines. Example 11 describes assays for the involvement of ICAM-R in homotypic cell-cell adhesion.

EXAMPLE 1

Nucleic acid and amino acid alignments of individual sets of CAMs (e.g., ICAM-1 and ICAM-2) did not manifest sufficient conservation between molecules to yield information useful in the design of consensus-type probes for isolating related novel genes. The strategic focus of attempts to isolate unknown DNAs encoding cellular adhesion molecules therefore involved the development of degenerate consensus oligonucleotides representing putative spaced apart DNA sequences of various known molecules and the use of these oligonucleotides as primers for polymerase chain reaction (PCR) amplification of DNA replicas of intermediate gene sequences which resemble, but are not identical to, the known DNAs. The starting point for oligonucleotide primer design was the notation that the amino acids in regions surrounding cysteines which form immunoglobulin-like loops of certain CAMs are somewhat conserved. At the amino terminal side of the motif, the sequence (SEQ ID NO: 3)

G-X-X-(V or L or I)-X-(V or L or I)-X-C is found, while at the carboxy terminal side of the motif, the sequence (SEQ ID NO: 4)

N-X-G-X-Y-X-C-X-(V or A)

is typical. [See Hunkapiller et at., *Nature*, 323:15–16 (1986); Williams et at., *Ann. Rev, Immunol.*, 6:381–405 (1988); and Newman et at., supra.] In and of themselves the two amino acid motifs are much too general and do not allow the construction of degenerate sets of oligonucleotides useful as probes for unknown DNAs which might share the motif. In an attempt to solve this problem, each individual CAM sequence was split into a domain of sub files defined by the cysteine motif termini described above. Subfiles were generated for each of the seven domains of human vascular adhesion molecule (VCAM-1), the six domains of human platelet endothelial cell adhesion molecule (PECAM-1), the five domains of ICAM-1, the two domains of ICAM-2, three of the four domains of both human myeloglobin related glycoprotein and human fibroblast growth factor receptor, and the five domains of mouse neural cell adhesion molecule. All the subfiles were pooled and segregated independently from the CAM of origin using a multialignment homology computer algorithm designated "Multalin" Corpet, *Nucleic Acids Research*, 16(22):10881–10890 (1988)] providing a tree of alignment allowing the ascertainment of consensus sequences around cysteine motifs. A consensus sequence representing the amino terminal cysteine motif was determined as (SEQ ID NO: 5)

G-K-(N or S)-(L or F)-T-(L or I)-(R or E)-C, while the carboxy terminal consensus sequence was determined as (SEQ ID NO: 6)

(D or E)-(H or D)-(H or G)-(G or H)-(A or R)-N-F-S-C.

Employing human preferences for codon usage to partially eliminate degeneracy, three separate sets of oligonucleotides totalling 1152 probes were generated for use as top strand PCR primers for amplification from a putative amino terminus of the motif. The specific degenerate sequences of the three pools are set out below and respectively in SEQ ID NOS: 7, 8 and 9.

```
5'-ATTCTGCAGGCAAGAACCTGACCCTGCGCTG-3'
        A    T    C      AA  CA  G
                              T   T
```

-continued

```
5'-ATTCTGCAGGCAAGAGCTTCACCCTGGAGTG-3'
         A  T  T    AA C     A
                       T  T

5'-ATTCTGCAGGCAAGTCCTTCACCCTGGAGTG-3'
         A  T  T   AA C      A
                      T  T
```

Each of the primers was provided with DNA comprising a PstI restriction endonuclease recognition site (CTGCAG) to facilitate cloning of amplified products.

A total of 768 probes were designed as bottom strand primers as set out below (and in SEQ ID NOS: 10 and 11) for amplification from a putative carboxy terminus of the motif. Each of these primers was provided with an XbaI recognition site (TCTAGA) to facilitate cloning of amplified products.

```
5'-ATTTCTAGAGAAGTTGGCGCCGTGGTGGTC-3'
            A   A  A  C   A  A CA

5'-ATTTCTAGAGAAGTTGCGGTGGCCGTGGTC-3'
            A   A   C TA   C   A CT
```

Oligonucleotides were synthesized with an automated Applied Biosystems (Foster City, Calif.) (Model 394) DNA synthesizer using an 0.2 micromolar scale synthesis program and employing beta-cyanoethyl chemistry. Protective groups were then removed by heating at 55° C. for in excess of six hours. Oligonucleotides were then lyophilized to dryness, rehydrated in 10 mM Tris, pH 7.0, 1 mm EDTA(TE) and desalted in TE by size exclusion chromatography with G25-150 Sephadex.

EXAMPLE 2

The two sets of probes whose design and synthesis are described in Example 1 were employed in PCR amplification procedures applied to a human genomic DNA template. Briefly put, PCR-generated fragments of a size similar to that of the immunoglobulin-like loop regions of ICAM-1 and ICAM-2 were isolated, subcloned into Bluescript plasmid and screened both directly and by sequencing in arrays for hybridization with ICAM-1 and ICAM-2 DNA. Approximately 50% of the fragments were identical with ICAM-1 or ICAM-2 (except, of course, in the regions of the degenerate primer). One subclone, designated 13-3C7, was found to have an open reading frame homologous to ICAM-1 and ICAM-2 in the region of their respective second domains. It did not correspond to any known sequence present in the Genbank data base. The specific manipulations leading up to the isolation of subclone 13-3C7 were as follows.

The degenerate oligonucleotides were mixed to a final concentration of 10 ug/ml in a PCR reaction to amplify human genomic DNA obtained either from peripheral blood leukocytes or Hela cells. The DNA amplification was performed in 2 mM $MgCl_2$, 25 mM KCl, 10mM Tris pH 8.3 PCR buffer with 2 mM deoxynucleotides. After a 94° C. denaturation for 4 min, 35 cycles were performed with an annealing at 60° C. for 2 min, elongation at 72° C. for 4 min and denaturation at 94° C. for 1 min. A DNA band migrating at about 0.2 kb was extracted from a 6% polyacrylamide gel by electroelution, digested by XbaI and Pst 1 restriction enzymes, and ligated into the Bluescript vector (Stratagene Corp., La Jolla, Calif.). The plasmid was electroporated into XL 1-blue strains of E. coli (Stratagene) and colonies were selected on X-gal IPTG, carbenicillin agarose plates. Single strand templates were obtained from 6 white colonies after addition of M13K07 helper phage (Stratagene), carbenicillin, and kanamycin to a 2 ml culture of each colony. For sequence analysis, the single strand templates were then sequenced using the Sanger method both by DNA automatic sequencing (Applied Biosystems Inc.) and with a sequenase kit (UCB, Belgium). Four sequences (clones 1.1, 1.3, 1.4, 1.6) were obtained which were 184–185 base pairs long and were 92–95% homologous to the second domain of ICAM-2. In addition, a 182 base pair long DNA sequence (clone 1.5) was obtained which contained a frameshift in the open reading frame of an ICAM1-like domain along with a 66 base pair DNA (clone 1.2) corresponding to a truncated immunoglobulin-like domain.

The sequence of clones 1.6, 1.5, 1.2 was used to design three oligonucleotide probes (RM16, RM15, RM12) that were used in subsequent tests to eliminate from further consideration additional colonies containing cDNAs that were highly homologous to the previous isolated clones. The sequence of probes RM16, RM15 and RM12 (SEQ ID NOS: 12, 13 and 14, respectively) is set out below.

RM16   GAGACTCTGCACTATGAGACCTTCG

RM15   CAGGTGATTCTCATGCAGAGTCCAGG

RM12   CCGACATGCTGGTAAGTGTGTCCAA

In a second round of tests, new colonies were obtained from the original PCR products that had been XbaI and Pst 1 digested and from additional PCR products that had been rendered blunt-ended by treatment with the Klenow fragment of polymerase I and subcloned by blunt-end ligation. The colonies containing the vector with an insert were selected on carbenicillin L broth agarose plates containing X-gat and IPTG. Single strand templates were then synthesized in 96 wells plates by growing individual white colonies in 300 ul L broth, in which we added M13K07 phage, carbenicillin and kanamycin. Ten ul of each template were transferred with a pronging device to a nylon membrane, denatured and fixed with UV light. We transferred 10 ul of each template on three different nylon membranes for each 96 well plate. Oligonucleotides RM16, RM15, RM12 were labelled by phosphorylation using 32p gamma-ATP. The nylon membranes were pre-hybridized in 20% formamide, 5× SSC, 5× Denhardt solution and 0.5 % SDS for 3 hours at 42° then hybridized overnight with the different radiolabelled oligonucleotide probes under the same condition. The membranes were then washed in 0.2× SSC, 0.5% SDS three times for 15 min each at room temperature then washed in the same buffer at 37° C. for 15 min, rinsed in 2× SSC and exposed. Each template that did not hybridize with either of the three oligonucleotide probes was further sequenced using the Sanger technique by DNA automatic sequencing and by sequenase kit. Using this technique, the 170 base pair DNA sequence of clone 13-3C7 was determined.

EXAMPLE 3

The cDNA insert of subclone 13-3C7 isolated in Example 2 was used as a hybridization probe to screen four different lambda phage cDNA libraries prepared from human spleen, human placenta (two libraries) and human leukocyte cell line U937 (ATCC #CRL 1593). Briefly summarized, one hundred and twenty positive clones were picked (from among the approximately 1.6 million clones screened), subcloned, rescreened with the 13-3C7 probe, and the rescreening positives were size selected for inserts of greater than approximately 500 base pairs by analytical PCR with primers corresponding to the plasmid DNA flanking the insertion for DNAs. A 1.3 kb clone, designated clone 19C and derived from U937 cDNA, was sequenced and revealed DNA regions encoding two immunoglobulin-like domains separated by what appeared to be an intervening sequence (intron) resulting from improper or incomplete mRNA splicing prior to cDNA formation. The two regions displayed significant homology, but overall distinctness, in comparison to domains 2 and 3 of ICAM-1 and less homology to domains 1 and 2 of ICAM-2.

The specific procedures leading up to isolation of clone 19C were as follows. The four libraries were constructed in lambda GT 10 phage using cDNA obtained from the U937 cell line, from the spleen of a patient with chronic myelomonocytic leukemia and from human placenta. Exact match oligonucleotides designated 1 Hr-5' and 1Hr-3' were designed corresponding to the 5' and 3' sides of the domain-like region of subclone 13-3C7 (including bases attributable to incorporation of the original degenerate primer). The sequences of the 1 Hr-5' and 1 Hr-3' oligonucleotide primers are set out below and respectively in SEQ ID NOS: 15 and 16.

```
1 Hr-5'   GACCATGAGGTGCCAAG

1 Hr-3'   ATGGTCGTCTCTGCTGG
```

Using these oligonucleotides in a PCR reaction with the 13-3C7 insert template and P32 dCTP, a 148 bp long DNA probe was generated. The cDNA libraries were plated and transferred on nylon membranes. They were pre-hybridized in 40% formamide, 5× SSC, 5× Denhardt, 0.5% SDS at 42° C. for at least 15 minutes, then hybridized overnight with the probe in the same buffer at 42° C. The membranes were washed several times at room temperature in 2× SSC and exposed. Most of the phage plaques that hybridized with the probe were derived from the U937 cDNA library. These phages were further purified and tested by PCR (using 1 Hr-5' and 1 Hr-3' as primers) for the presence of the domain inside the cDNA clones. They were also tested by PCR to determine the length of the clones and the location of the domain within the cDNA fragment (using a combination of 13-3C7 specific primers and primers homologous to flanking gt10 vector sequences). Two clones were selected. Clone 1F was 0.7kb long and clone 19C was 1.3 kb long. The cDNAs were digested with EcoR1 and subcloned in the Bluescript vector. In addition, the largest cDNA (clone 19C) was sonicated to obtain small pieces which were sub-cloned into Bluescript for sequencing. By homology with the ICAM-1 molecule, clone 19C cDNA contains 2 regions having homology to domains 2 and 3 of ICAM-1 respectively with an intervening sequence of unrelated DNA. Hereinafter, these DNA regions are referred to as domain 2 and domain 3 of ICAM-R.

EXAMPLE 4

The 1.3 kb (clone 19C) DNA isolated in Example 3 and having regions encoding immunoglobulin-like loops resembling domains 2 and 3 of ICAM-1 was then employed to generate a probe for the screening of additional cDNA libraries in an attempt to isolate a full length cDNA clone. Briefly, the domain 2 and 3 regions within clone 19C were each amplified by PCR using unique probes designated to match respective amino (5') and carboxy (3') terminal portions of the domains. These amplified DNAs, in turn, provided probes for screening of cDNA libraries derived from: (1) the HL60 myelomonocytic cell line; (2) lipopolysaccharide-activated human monocytes; (3) the HUT-78 T-cells (ATCC #T1B161); and (4) activated peripheral blood leukocytes. The latter two libraries yielded no positives upon rescreening. Positives derived from HL60 and monocyte cDNA libraries were then screened with a probe representing of domain 2 of ICAM-1 DNA (GenBank, Accession No. 22634) in order to eliminate ICAM-1 clones. A single phagmid clone derived from lambda 345 and designated pVZ-147, repeatedly tested positive for hybridization with the probe(s) based on the DNA isolated in Example 4 and negative for hybridization with the ICAM-1 DNA probe. The approximately 1.7 kb insert from clone pVZ-147 was isolated and sequenced to provide the 1781 base pair sequence set out in SEQ ID NO: 2. The deduced amino acid sequence of the polypeptide encoded by this DNA is set out in SEQ ID NO: 1. The polypeptide was designated "ICAM-R" on the basis of its structural relatedness to ICAM-1 and ICAM-2.

The specific manipulations involved in the isolation of lambda phage clone pVZ147 are as follows. All cDNA libraries were constructed in phage lambda GT10 except for the HL60 library which cloned into phage lambda 345. Oligonucleotides for use in library screening and rescreening included:

(a) probe IHr2-5' (SEQ ID NO: 17) TTCACCCTGCGCTGCCAA;

(b) probe IHr2-3' (SEQ ID NO: 18) AAAGGGGCTCCGTGGTCG;

(c) probe IHr 3-5' (SEQ ID NO: 19) CCGGTYCTTGGAGGTGGAA;

(d) probe IHr 3-3' (SEQ ID NO: 20) CATGACTGTCGCATICAGCA;

(e) probe Icam 1-5 (SEQ ID NO: 21) GCAAGAACCTYACCCTAC; and, (f) probe Icam 1-3 (SEQ ID NO: 22) GAAATTGGCTCCATGGTGA. Probes IHr 2-5' and IHr 2-3' were employed in a PCR amplification using P32dCTP on the clone 19C template to generate a domain 2 specific probe for cDNA screening. Likewise, probes IHr 3-5' and IHr 3-3' were employed to generate a domain 3 specific probe. Finally, probes Icam 1-5 and Icam 1-3 were employed to amplify an ICAM-1 segment probe corresponding to bases 440 through 609 of the ICAM-1 cDNA sequence (GenBank, Accession No. 22634) i.e., the I C AM- 1 second domain.

The cDNA libraries were plated, transferred on nylon membranes, hybridized with the domain 2 probe in 40% formamide, 5× SSC, 5× Denhardt, 0.5% SDS and washed as described above. All the plaques that hybridized with the domain 2 probe were derived from the monocyte and HL60 libraries. These phage plaques were purified by dilution, plating, transfer and hybridization with the domain 2 probe. To further characterize the cDNA clones, each plaque that had hybridized with the domain 2 probe was grown on an array in triplicate, transferred to a nylon membrane and hybridized under higher stringency conditions (50% formamide, 5× SSC, 5× Denhardt, 0.5% SDS) with three different probes the domain 2 probe; the domain 3 probe, and the ICAM-1 second domain probe. Six clones were found in the HL60 library and 2 clones in the monocyte library which hybridized with both domain 2 and domain 3 probes and not the ICAM-1 second domain probe. The cDNA of the 6 clones from the HL60 library were further analyzed. The phages were tested by PCR for the presence of properly spliced cDNA using oligonucleotide primers corresponding to the 5' extremity (IHr2-5') of domain 2 and to the 3' extremity (IHr3-3') of domain 3. The clones were also tested by PCR for length and location of the domains inside the clones. The cDNA plasmids were extracted and cyclized from phage lambda 345 by digestion with SfiI and self-ligation. To facilitate making single strand templates and sequencing in both orientations, each cDNA was also subcloned in bluescript SK+vector. Plasmid pVZ147 was determined to include the entire ICAM-R coding sequence in a single open reading frame.

EXAMPLE 5

A. Characterization of the ICAM-R Polypeptide

FIG. 1 graphically illustrates the sequence of the cDNA insert of the lambda phage clone pVZ 147 isolated in Example 4, above. The total of 1781 bases shown are as set out in SEQ ID NO: 2. The deduced amino acid sequence of the ICAM-R polypeptide as set out in SEQ ID NO: 1 is graphically subdivided in the FIGURE into the following regions:

(1) A putative signal or leader sequence is illustrated preceding the sequence of the "mature" protein and spanning amino acids designated −29 through −1. Determination of whether the translation product is actually initiated at −29 or −26 will be provided by amino acid sequencing of intracellular expression products. The designation of the first residue of the mature protein was based on generalized analogy to amino acids (and corresponding bases) for residues of secreted human proteins in the region of the junction of the mature protein and leader sequences. Confirmation of the actual initial residue of the mature protein awaits sequencing of a secreted recombinant product or, e.g., an immunopurified natural product.

(2) Within the mature protein spanning residues +1 through 518, five putative immunoglobulin-like loop regions are shown (white on black) bounded by cysteines within the five putative immunoglobulin-like domains (shown in boxes). Note that in the first domain (residues 1 through 91), cysteine residues potentially significant to loop formation are present at positions 24, 28, 67 and 71. Each of the remaining putative loops has a single relevant cysteine at each of its ends.

(3) Also within the mature protein, a putative hydrophobic "transmembrane" region is illustrated with dashes connecting residues 457 through 481 which follow the fifth immunoglobulin-like domain. A putative carboxy terminal "cytoplasmic" region constitutes residues 482 through 518.

(4) Potential N-linked glycosylation sites [characterized by the consensus sequence, Aspargine-X-(Serine or Threonine)] are indicated with an asterisk. Potential O-linked glycosylation sites occur at any serine or threonine residue.

A comparison was made between the amino acid sequence (SEQ ID NO: 1) of ICAM-R and the published 537 residue amino acid sequence of ICAM-1 (GenBank Accession No. 22634; cf, FIG. 8 of European Patent Application 0 289 949 published Nov. 11, 1988). This comparison revealed 49 matches within the aligned 537 residues, indicating an overall amino acid homology of 46% between the two polypeptides. The highest percentage of matches was noted to be present in domains 2 and 3 of ICAM-1 and putative domains 2 and 3 of ICAM-R. Likewise the alignment of SEQ ID NO: 1 with the published 295 residues of the amino acid sequence of ICAM-2 (GenBank accession No. 22635; cf, FIG. 2 of European Patent Application 0 387 668 published Sep. 19, 1990) revealed 78 matches among the 282 aligned residues, for a 27% overall homology of amino acids.

B. Characterization of ICAM-R DNA

A comparative alignment of the ICAM-R DNA sequence (SEQ ID NO: 2) was made with the published DNA sequences of ICAM-1 and ICAM-2, supra. A total of 677 matches were noted among the 1623 aligned bases of ICAM-R and ICAM-1 providing an overall homology of 41%. A 42% homology (484 matches) between the aligned 1136 bases of ICAM-R and ICAM-2 DNAs was noted.

Reference points in the FIG. 1 DNA having "historical" significance to the isolation of the ICAM-R gene include the following:

(a) bases 420 through 567 correspond to the subclone 13-3C7 isolated in Example 2;

b) bases 373 through 663 correspond to the immunoglobulin-like domain 2 localized in clone 19C of Example 3 (with bases 4 18 through 435 and 561 through 578, respectively corresponding to probes IHr2-5' and IHr2-3' employed for PCR amplification of domain 2 to provide one of the oligonucleotide probes for use in Example 4); and (c) bases 664 through 957 correspond to the immunoglobulin-like domain 3 localized on clone 19C of Example 3 (with bases 699 through 717 and 800 through 819, respectively corresponding to probes IHr3-5' and IHr3-3' employed for PCR amplification of domain 3 to provide another oligonucleotide probe for use in Example 4.

EXAMPLE 6

ICAM-R cDNA was transfected into L-M(TK⁻) mouse cells (ATCC Accession #CCL 1.3) and the cells were assayed for expression of ICAM-R by northern blot and in situ hybridization.

A. Transfection of ICAM-R DNA

The full length ICAM-R cDNA insert of pVZ-147 and a small portion of the phagmid vector 3' to the cDNA insert was excised using NotI and XbaI and ligated into commercial plasmid pCDNA1-neo (Invitrogen Inc., San Diego, Calif.) cut with NotI and XbaI. The resulting plasmid, designated pCDNA1-neo-ICAM-R, was transfected into mouse L cells by the calcium phosphate precipitation method described in Chen and Okayama, *Molecular and Cellular Biology*, 7, 2745–2748 (1987). ICAM-1 DNA was transfected into mouse L cells as a control. A cDNA fragment containing the complete ICAM-1 protein coding region was ligated into plasmid pCDNA 1-neo and transfected into L cells by the calcium phosphate precipitation method. Following selection for neomycin resistance, individual ICAM-R or ICAM-1 transfectants were subcloned by limiting dilution.

B. Northern blot hybrozations

Following transfection of full length ICAM-R or ICAM-1 cDNAs into mouse L cells, specific expression of the corresponding mRNAs in transfected and untransfected L cells was determined by northern blot hybridization with $^{32}$P-labelled ICAM-R or ICAM-1 DNA probes. Transfectants were grown in log phase, then centrifuged and washed two times with 150 mM NaCl. The pellet was resuspended in 3.5 ml GIT (guanidinium isothiocyanate) buffer, then sheared in a polytron mixer for 20 seconds. After adding 1.7 ml CsCl Buffer to an ultracentrifuge tube, the GIT/RNA mix was layered on top. Samples were spun at 35 K (179,000×g), 20° C., for 21 hours. All liquid was removed and the pelleted RNA was resuspended in 300 μl 0.3M Na Acetate pH 5.2, then precipitated with 750 μl EtOH at −20° C. The precipitate was resuspended in $H_2O$, then treated with Proteinase K to remove any RNAses. After a phenol/chloroform extraction, the RNA was re-precipitated, resuspended in $H_2O$ and the OD at 260 nm measured.

The RNAs were electrophoresed in 1% formaldehyde agarose gels, prepared with diethyl pyrocarbonate (DEPC) treated solutions. 10 μg of each total RNA sample was loaded per lane. After adding 25 μl sample buffer, the samples were heated to 65° for 15 minutes. 1 μl ethidium bromide (1 mg/ml) was added prior to loading the gel. RNA was electrophoresed at 30 V for approximately 18 hours with continuous circulation of buffers accomplished with a peristaltic pump. Each resulting gel was soaked two times in 20× SSPE for 20 minutes each at room temperature. Transfer of RNA to Hybond-C membranes (Amersham, Arlington Heights, Ill.) was accomplished by capillary action overnight in 20× SSPE. Using a Stratagene stratalinker, RNA was stably crosslinked to each membrane by exposure to ultraviolet light.

To generate ICAM-1 DNA probes, 100–200 ng template DNA (a 1.8 kb Xba/Kpn fragment incorporating the entire ICAM-1 coding sequence) was mixed with $H_2O$ and random hexamer, boiled for 5 minutes, and then incubated 5 minutes on ice. The following were added: $^{32}$PdCTP and $^{32}$PdTTP, $10^{-4}$M dGTP/dATP, 10× Klenow Buffer (Boehringer Mannheim, Indianapolis, Ind.) and Klenow enzyme, and the mixture was left at room temperature for 1 hour. Samples were passed over a Boehringer Quickspin G25 DNA column to separate incorporated from unincorporated label.

To generate ICAM-R DNA probes, 200 pg of DNA template (a 1.4 kb fragment of clone pVZ-147 truncated to remove the poly-A tail) was amplified by PCR primed with oligonucleotides complimentary to the 5' and 3' extremities of domain 1. $^{32}$P-dCTP was added to the reaction mixture. Samples were held at 94° C. for 4 minutes then run through 30 cycles of the temperature step sequence (94° C., 1 minute; 50° C., 2 minutes; 72° C., 4 minutes) Samples were then run over a Quickspin column and incorporation of label was assessed by scintillation counting of 1 μl aliquots.

The DNA probes were denatured with 5M NaOH, then neutralized with 1M Tris. The Hybond membranes were prehybridized at 50° C. for 30 minutes in a 50% formamide pre-hybridization mix. Probe was added to each membrane to a concentration of $1\times10^6$ dpm/1 ml hybridization mix (50% formamide, 5× Denhardt's solution, 5× SSPE, 1% SDS), and the membranes were incubated overnight at 42° C. Each membrane was then washed in 2× SSPE/0.1% SDS at room temperature 5 times for 10 minutes each. One 10 minute wash was done at 50° C. in 0.5× SSPE/0.1% SDS, with an additional rinse in 2× SSPE. Hybridization with the major RNA transcript was quantitated using a Molecular Dynamics (Sunnyvale, Calif.) Model 400A PhosphorImager.

Figure 2B:
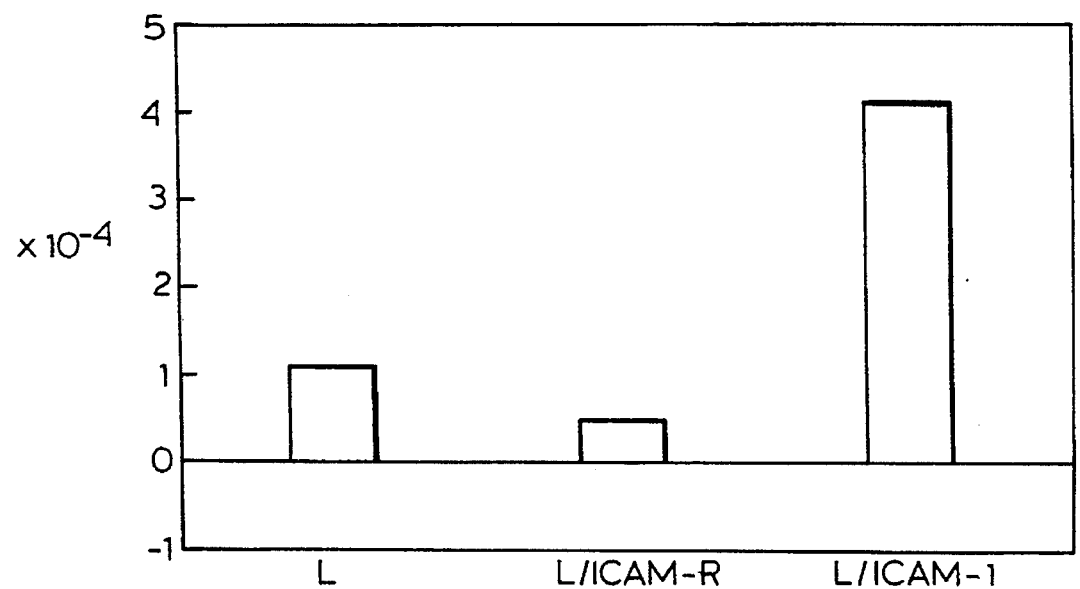
Figure 3A:
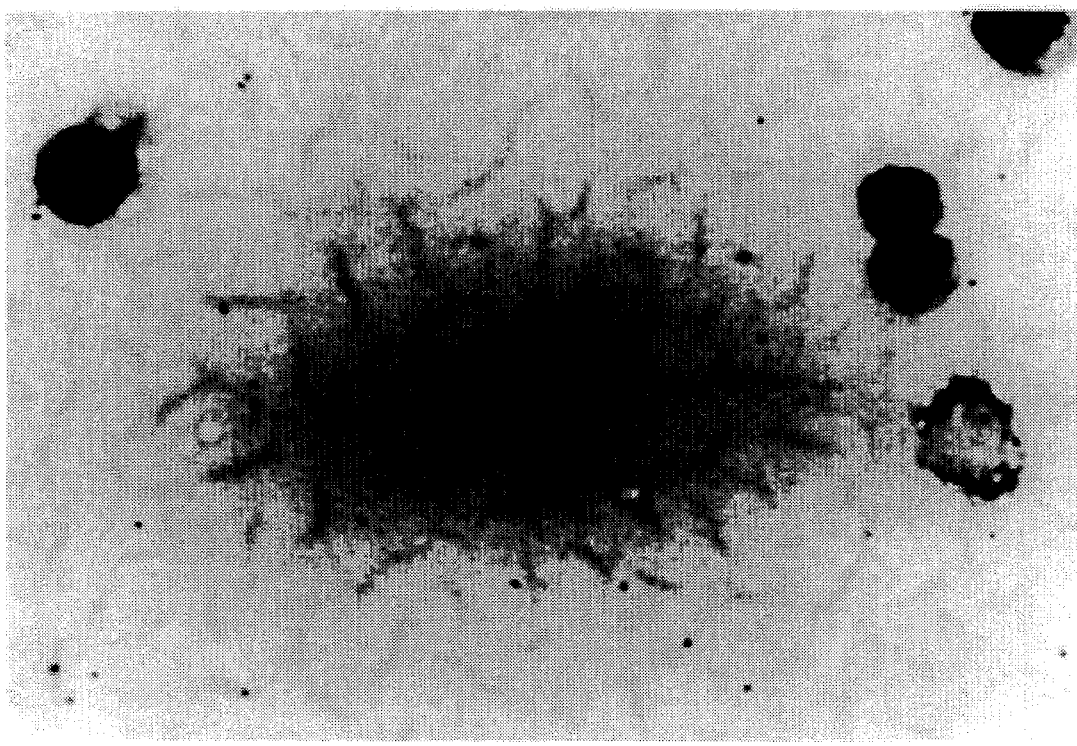
Figure 3B:
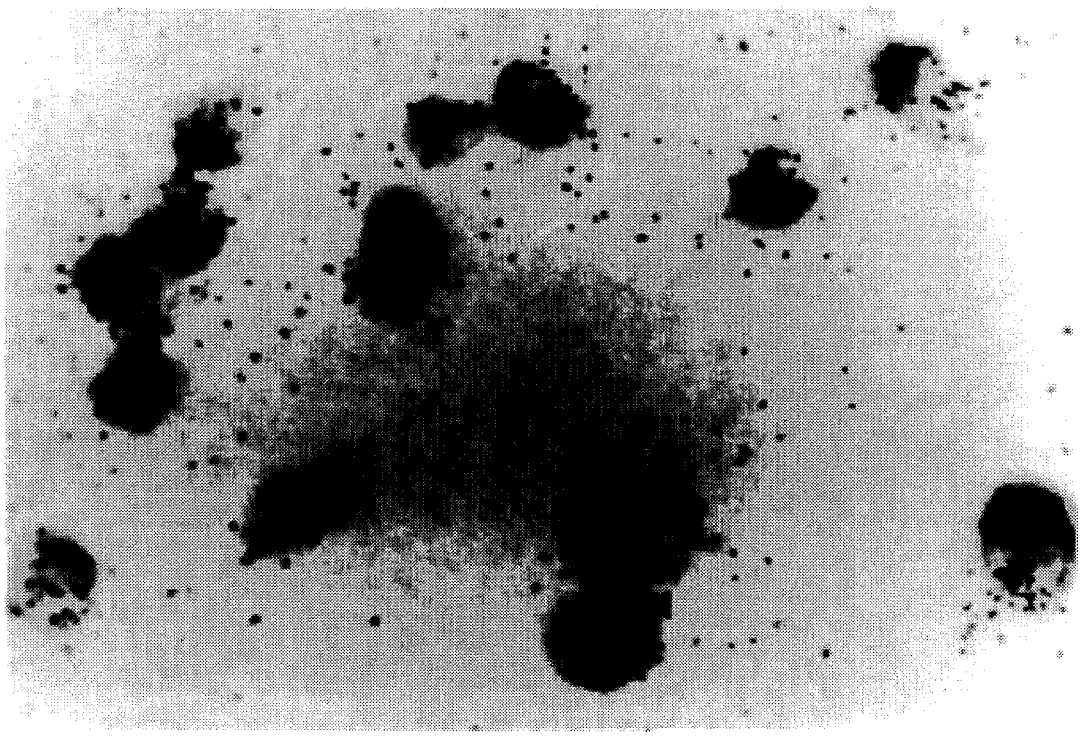
Figure 3C:
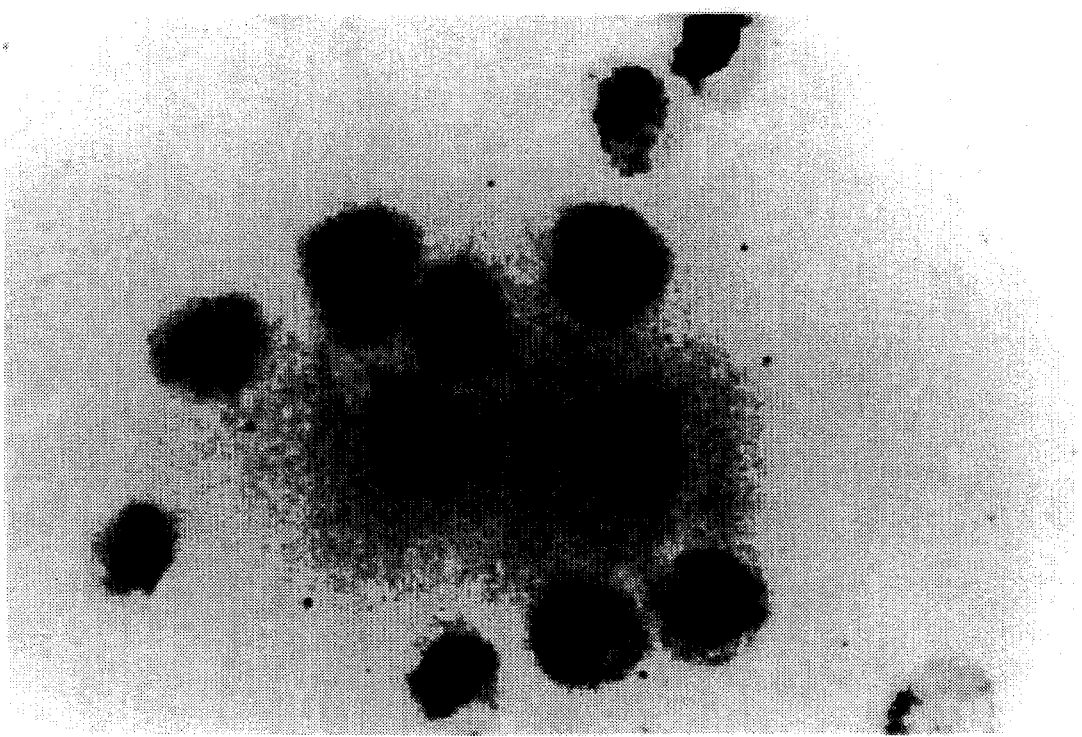
Figure 3D:
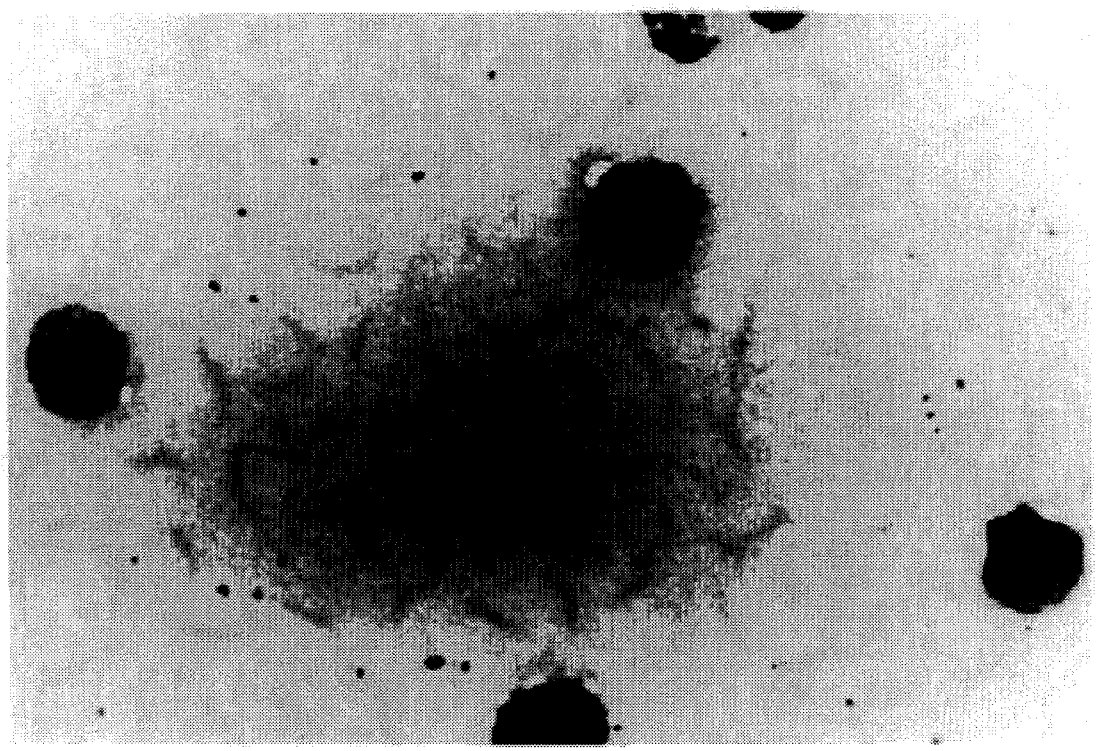
Figure 3E:
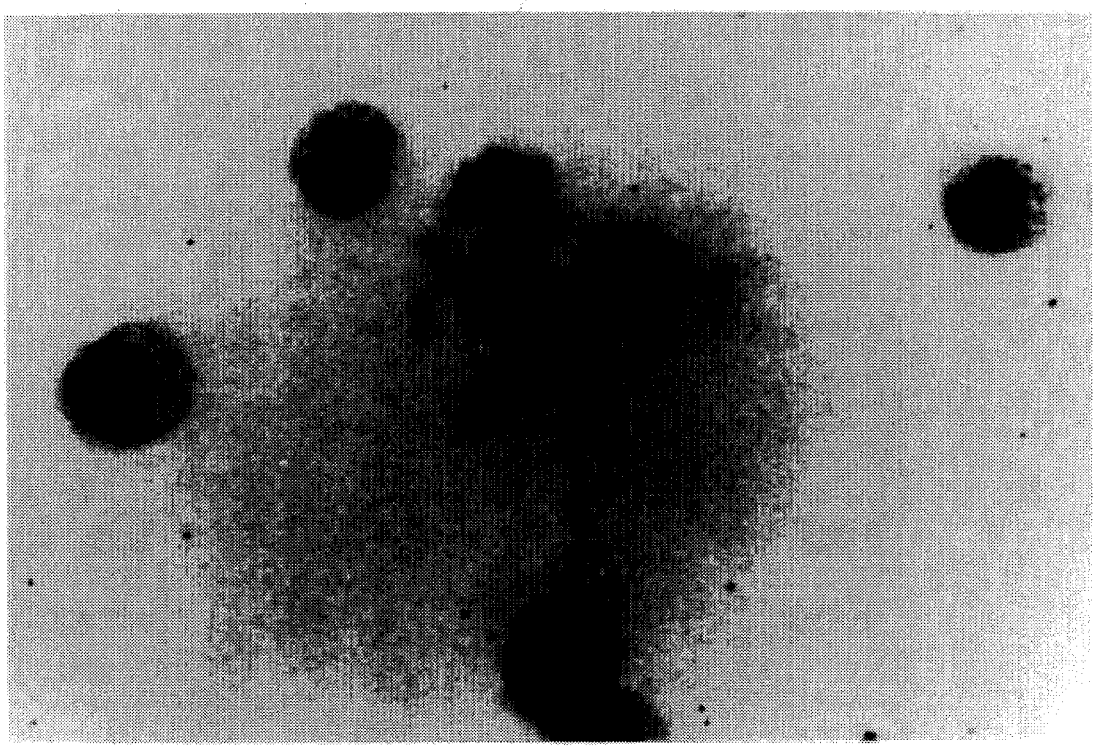
Figure 3F:
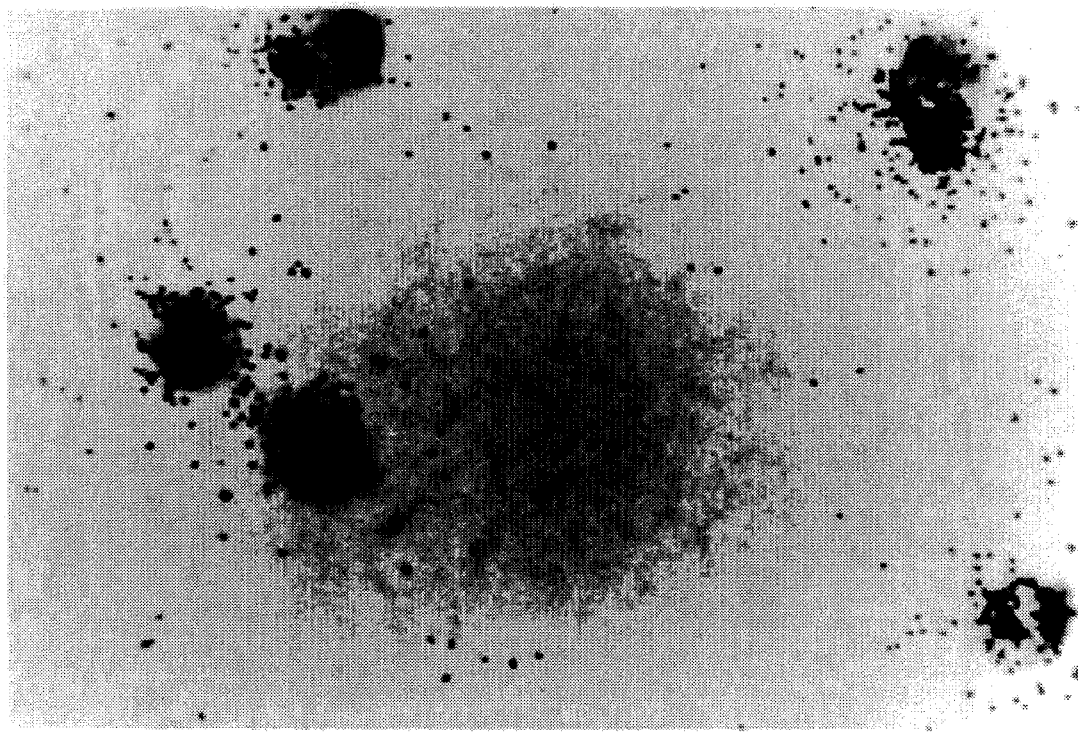

Results of the northern blot hybridizations are presented in bar graph form in FIG. 2(A through B). FIG. 2A illustrates specific hybridization of the ICAM-R probe with RNA extracted from ICAM-R transfectants, but not with RNA from ICAM-1 transfectants or untransfected L cells. Reciprocally, FIG. 2B indicates hybridization of the ICAM-1 probe with RNA extracted from ICAM-1 tranfectants, but not with RNA from ICAM-R transfectants or the parental L cells.

C. In situ Hybridizations

L cells and L cells transfected as described above with either ICAM-R or ICAM-1 cDNAs were hybridized in situ with radiolabelled single strand RNA probes derived from ICAM-R or ICAM-1. Single-stranded RNA probes were generated from DNA templates corresponding to the first (i.e., N-terminal) domain of ICAM-R or ICAM-1 by in vitro RNA transcription incorporating $^{35}$S-UTP. Probes were chemically hydrolyzed to approximately 200 bp.

Transfected and untransfected L cells were layered onto Vectabond (Vector) coated slides and stored at −70° C. Prior to use, slides were removed from −70° C. and placed at 55° C. for 5 minutes. Sections were then fixed in 4% paraformaldehyde for 20 minutes at 4° C., dehydrated in 70–95–100% EtOH for 10 minutes at room temperature, and then allowed to air dry for 30 minutes. Sections were denatured for 2 minutes at 70° C. in 70% formamide/2× standard sodium citrate (SSC), rinsed in 2× SSC dehydrated and then air dried for 30 minutes. Sections were prehybridized for 2 hours at 42° C. with a mixture containing 50% formamide, 0.3M NaCl 20 mM Tris pH 8.0, 10% dextran sulfate, 1× Denhardt's solution, 100 mM dithiothreitol (DTT) and 5 mM EDTA. Hybridization was carried out overnight (12–16 hours) at 50° C. in the same mixture additionally containing $^{35}$S labelled either ICAM-1 or ICAM-R RNA probes ($6\times10^5$ cpm/section). After hybridization, sections were washed for 1 hour at room temperature in 4× SSC/10 mM DTT, then for 40 minutes at 60° C. in 50% formamide/1× SSC/10 mM DTT, 30 minutes at room temperature in 2× SSC, and 30 minutes at room temperature in 0.1× SSC. Sections were alcohol dehydrated and air dried for 30 minutes.

Air dried slides were dipped in Kodak NTB2 Nuclear Emulsion (heated to 42° C.) and allowed to air dry for 2 hours at room temperature in complete darkness. Slides were stored at 4° C. in complete darkness until time of development. Slides were then placed in Kodak D 19 developer for 4 minutes at 4° C., dipped 4 times in Acid Stop (1 ml glacial acetic acid/500 ml $dH_2O$) and then placed in Kodak fixer for 4 minutes at 4° C. The slides were rinsed 3 times in tap water, and counterstained with hematoxylin/eosin.

Photomicrographs of the in situ hybridizations are set out in FIG. 3(A through F) wherein photomicrograph 3A is of parental L cells probed with ICAM-R RNA; 3B is of ICAM-R transfected L cells probed with ICAM-R RNA; 3C is of ICAM-1 transfected L cells probed with ICAM-R RNA; 3D is of parental L cells probed with ICAM-1 RNA; 3E is of ICAM-R transfected L cells probed with ICAM-1 RNA; and 3F is of ICAM-1 transfected L cells probed with ICAM-1 RNA. The photomicrographs demonstrate specific hybridization of each RNA probe only with L cells transfected with a homologous cDNA.

EXAMPLE 7

Six to twelve week old Balb/c mice (Charles River Biotechnical Services, Inc., Wilmington, Mass. IACUC #901103)were immunized with HL-60 cells to generate anti-ICAM-R monoclonal antibodies. Two Balb/c mice were bled retro-orbitally for the collection of pre-immune serum on day 0. On day 2, each animal received a total of $6\times10^6$ HL-60 cells in 0.5 ml PBS (0.1 ml s.c. and 0.4 ml i.p.). A second immunization with $9.5\times10^6$ HL-60 cells was administered on day 28 in the same manner. Immune serum was collected via retro-orbital bleeding on day 35 and tested by FACS to determine its reactivity to ICAM-R transfectants. Based on these results, both animals were immunized a third time on day 51 with $6.5\times10^6$ HL-60 cells (as before) and a fusion was performed with spleen cells from one animal (#764) on day 54.

The spleen from mouse #764 was removed sterilely. A single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 µg/ml streptomycin (RPMI)(Gibco, Canada). The cell suspension was filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from 3 naive Balb/c mice were prepared in a similar manner.

NS-1 myeloma cells, kept in log phase in RPMI with 11% fetal bovine serum (FBS)(Hyclone Laboratories, Inc., Logan, Utah) for three days prior to fusion, were centrifuged at 200 g for 5 minutes, and the pellet was washed twice as described in the foregoing paragraph. After washing, each cell suspension brought to a final volume of 10 ml in serum free RPMI, and 10 µl was diluted 1:100. 20 µl of each dilution was removed, mixed with 20 µl 0.4% trypan blue stain in 0.85% saline (Gibco), loaded onto a hemacytometer (Baxter Healthcare Corp., Deerfield, Ill.) and counted.

$2\times10^8$ spleen cells were combined with $4\times10^7$ NS-1 cells, centrifuged and the supernatant was aspirated. The cell pellet was dislodged by tapping the tube and 2 ml of 37° C. PEG 1500 (50% in 75 mM Hepes, pH 8.0)(Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supenatant, the pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5\times10^6$ thymocytes/ml. The suspension was dispensed into ten 96-well flat bottom tissue culture plates (Corning, United Kingdom) at 200 µl/well. Cells in plates were fed on days 2, 4, and 6 days post fusion by aspirating approximately 100 µl from each well with an 18G needle (Becton Dickinson), and adding 100 µl/well plating medium described above except containing 10 units/ml IL-6 and lacking thymocytes.

On day 8, culture supenatant were taken from each well, pooled by column or row and analyzed by FACS on parental L cells (negative control) and L cells transfected with ICAM-R DNA. Briefly, transfected and non-transfected L cells were collected from culture by EDTA (Versene) treatment and gentle scraping in order to remove the cells from the plastic tissue culture vessels. Cells were washed two times in Dulbecco's PBS without $Ca^{2+}$ and $Mg^{2+}$, one time in "FA Buffer" (D-PBS+1% BSA+10 mM $NaN_3$), and dispensed into 96-well round bottomed plates (Corning) at $1.5\times10^5$ cells/100 µl FA Buffer per well. At this point, the assay was continued at 4° C. Cells were pelleted by centrifugation in a clinical centrifuge at 4° C. The supenatant from each well was carefully suctioned off, the pellets were broken up by gently tapping all sides of the assay plate. 100 µl of hybridoma supenatant pool was added per well using a 12-channel pipetman. Each MAb-containing supenatant pool was incubated for 1 hour on both L parental and transfected cells at 4° C. Assay plates were then washed 2 times with FA Buffer leaving 150 µl final volume in each well. The plates were centrifuged and the resulting supenatant were carefully suctioned off as before. The last wash was replaced with 50 µl/well of a 1:100 dilution of a F(ab$^1$) fragment of sheep anti-mouse IgG (whole molecule)-FITC conjugate (Sigma, St. Louis, Mo.) prepared in FA Buffer. Assay plates were incubated at 4° C. (protected from light) for 45 minutes. The assay plates were then washed 2 times with D-PBS containing $NaN_3$ only (i.e., no BSA) in the same manner as before and the last wash was replaced with 200 µl/well 1% paraformaldehyde in D-PBS. Samples were then transferred to polystyrene tubes with the aid of a multichannel pipet for flow cytometric analysis (FACS) with a Becton Dickinson FACsan analyzer.

Supenatant from individual wells representing the intersecting points of positive columns and rows were rescreened by FACS the following day. Seven wells (designated 26E3D-1, 26E3E, 26H3G, 26H11 C-2, 26I8F-2, 26I10E-2 and 26I10F) showed preferential staining on the transfected L cells vs. the control L cells. These wells were cloned twice, successively, by doubling dilution in RPMI, 15% FBS, 100 µM sodium hypoxanthine, 6 µM thymidine, and 10 units/ml IL-6. Wells of clone plates were scored visually after 4 days and the number of colonies in the least dense wells were recorded. Selected wells of the first cloning were tested by FACS after 7 days. Activity was retained in four lines (26E3D-1, 26H11C-2, 26I8F-2 and 26I10E-2). The second cloning was tested 10 days after plating, and positive wells containing single colonies were expanded in RPMI with 11% FBS.

The monoclonal antibodies produced by hybridomas 26E3D-1, 26H11C-2, 26I8F-2 and 26I10E-2 were isotyped in a ELISA assay. Immulon 4 plates (Dynatech, Cambridge,. Mass.) were coated at 4° C. with 50 µl/well goat anti-mouse IgA,G,M (Organon Teknika) diluted 1:5000 in 50° C. mM carbonate buffer, pH 9.6. Plates were blocked for 30 minutes at 37° C. with 1% BSA in PBS, washed 3× with PBS with 0.05% Tween 20 (PBST) and 50 µl culture supernatant (diluted 1:10 in PBST) was added. After incubation and washing as above, 50 µl of horseradish peroxidase conjugated rabbit anti-mouse $IgG_1$, $G_{2a}$, $G_{2b}$, or $G_3$ (Zymed, San Francisco, Calif.) (diluted 1:1000 in PBST with 1% normal goat serum) was added. Plates were incubated as above, washed 4× with PBST and 100 µl substrate, consisting of 1 mg/ml o-phenylene aliamine (Sigma) and 0.1 µl/ml 30% $H_2O_2$ in 100 mM Citrate, pH 4.5, was added. The color reaction was stopped in 5 minutes with the addition of 50 µl of 15% $H_2SO_4$. $A_{490}$ was read on a plate reader (Dynatech). Results showed that the monoclonal antibody produced by hybridoma 26E3D-1 was $IgG_{2a}$, while the other three monoclonal antibodies were $IgG_1$.

Figure 4:
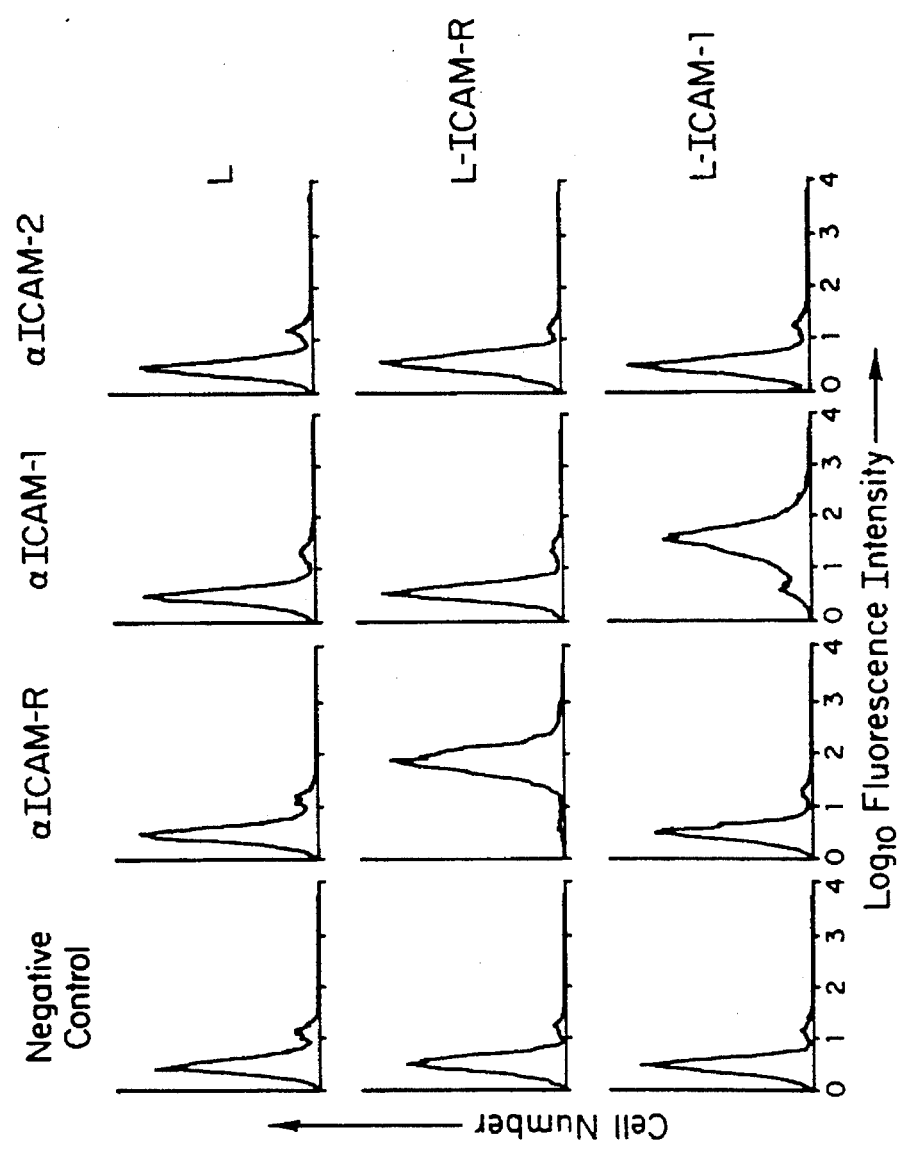

FACS analyses of indirect immunofluorescence staining of L cells and L cells transfected with ICAM-R, ICAM-1 or ICAM-2 DNA using monoclonal antibodies against ICAM-R, ICAM-1 and ICAM-2 were performed. Staining was carried out as described for FACS analyses above using either 0.1 ml hybridoma culture supernatant (anti-ICAM-R) or 1 µg pure monoclonal antibody (anti-ICAM-1 or ICAM-2) per $5\times10^5$ cells. Results of the analyses are presented as histograms (representing $10^4$ cells analyzed) in FIG. 4. Anti-ICAM-R antibody 26H11C-2 specifically bound to L cells transfected with ICAM-R cDNA, but not to parental or ICAM-1 transfected L cells. ICAM-R did not react with antibodies against ICAM-1 (Mab LB2 from Edward Clark, University of Washington) or ICAM-2 (Biosource Genetics Corp, Vacaville, Calif.). In parallel experiments, anti-ICAM-R monoclonal antibodies 26E3D-1, 26I10E-2, and 26I8F-2 exhibited the same reactivity on transfectants as monoclonal antibody 26H11C-2.

EXAMPLE 8

The distribution of ICAM-R and the expression of ICAM-R RNA were respectively assayed by FACS analysis and northern blot hybridization in various cell lines and normal cells.

A. FACS analyses of ICAM-R Distribution in Leukocytic Cell Lines and Normal Leukocytes FACS analyses carried out as described in Example 7 on leukocyte cell lines using anti-ICAM-R monoclonal antibodies, anti-ICAM-1 antibodies and anti-CD 18 antibodies illustrated that ICAM-R is expressed on a wide variety of in vitro propagated cells lines representative of the major leukocyte lineages, T lymphocytes, Blymphocytes, and myeloid cells. Surface expression of ICAM-R was not detected on the primitive erythroleukemic line, K562. Further, ICAM-R was not expressed detectably by cultured human umbilical vein endothelial cells (HUVECS) either before or after stimulation with tumor necrosis factor which did upregulate expression of ICAM-1. Table 1 below provides the mean fluorescence of each cell sample and the percent positive cells relative to a control in each cell sample (e.g., mean fluorescence of 13/11% positive cells).

TABLE 1

| Cell Type | Cell Line | ICAM1 | ICAMR | CD18 |
| --- | --- | --- | --- | --- |
| T cell | CEM | 13/11 | 212/99 | 160/99 |
| T cell | MOLT4 | ND | ND | 15/77 |
| T cell | HUT78 | 41/97 | ND | 110/99 |
| T cell | SKW3 | 9/36 | 293/99 | 82/99 |
| B cell | JY | ND | ND | 60/99 |
| B cell | JUOYE | 300/99 | 153/99 | 28/9 |
| B cell | RAJI | 229/99 | 98/96 | 51/98 |
| Mono | HL-60 | 53/89 | 146/100 | 159/100 |
| Mono | HL60-PMA | 88/99 | ND | 251/100 |
| Mono | U937 | 83/99 | 148/100 | 61/100 |
| Mono | U937-PMA | 68/100 | ND | 170/100 |
| Myelo | KG-1 | 32/84 | 587/99 | 239/99 |
| Myelo | KG-1a | 32/90 | 238/97 | 83/93 |
| Erythro | K562 | 37/0.84 | 31/0.27 | ND |
| Endo | Huvec | 51/18 | 57/1 | ND |
| Endo | Huvec-TNF | 278/99 | 36/1 | ND |
| Human | Lymphocytes | 31/19 | 388/99 | 305/99 |
| Human | Monocytes | 74/96 | 862/99 | 1603/99 |
| Human | Granulocytes | 12/40 | 323/99 | 376/99 |
| Monkey | Lymphocytes | 79/2 | 55/81 | 722/99 |
| Monkey | Monocytes | 98/1.7 | 162/95 | 1698/99 |
| Monkey | Granulocytes | 20/2 | 80/96 | 623/99 |

B. FACS Analyses of ICAM-R Distribution onHuman and Macaque T Cells

FACS analyses performed as described in Example 7 on normal human and macaque peripheral blood leukocytes showed that the four antioICAM-R monoclonal antibodies reacted with the three major human leukocyte lineages: lymphoid, monocytoid and granulocytoid. See the final six entries of Table 1. In addition, monoclonal antibody 26I10E-2 cross-reacted with macaque leukocytes indicating that this monoclonal antibody may be useful in monitoromg the expression of ICAM-R in disease models executed in this animal.

Figure 5A:
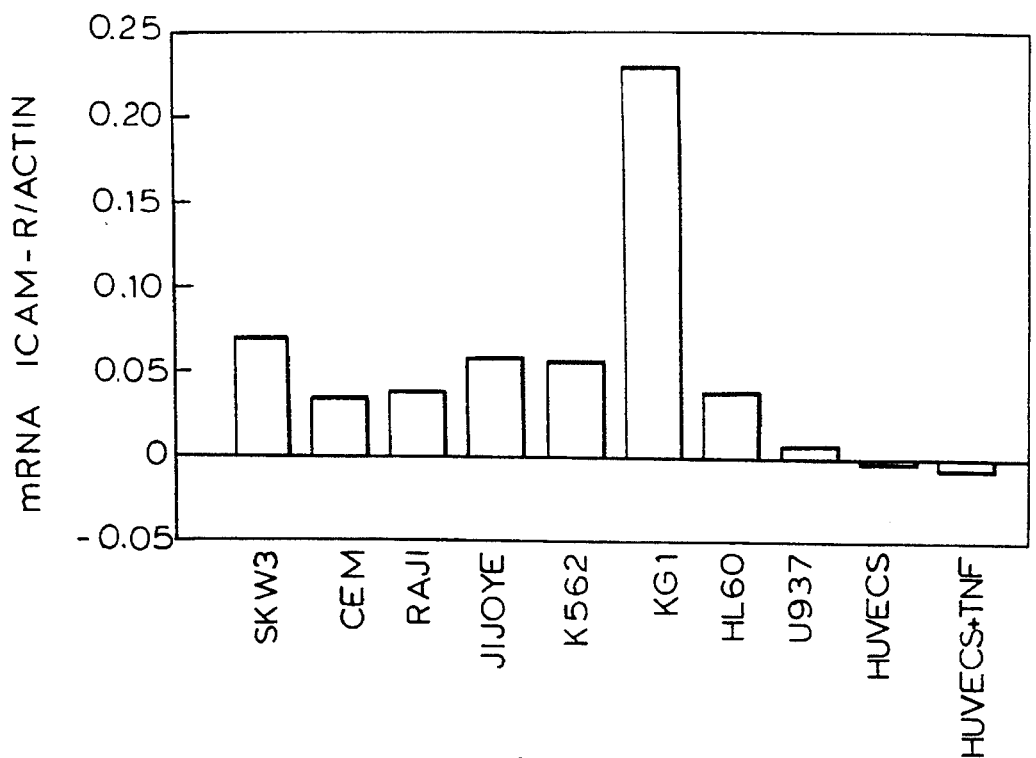
Figure 5B:
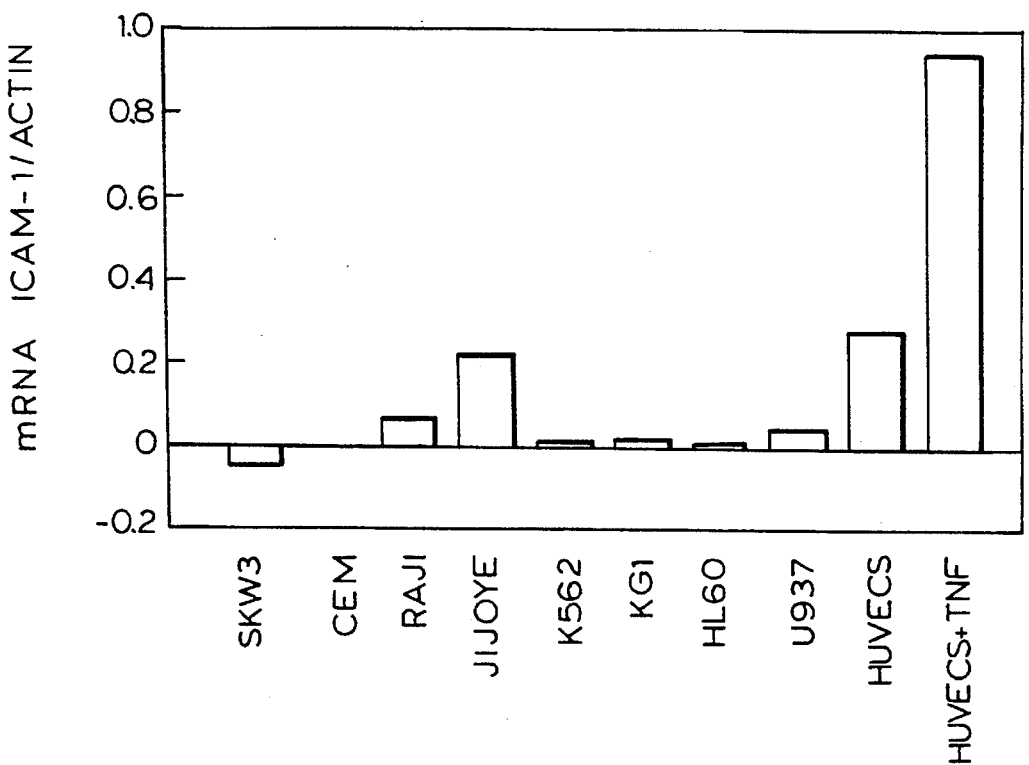

C. Northern Blot Analyses of ICAM-R RNA Expression in Leukocytic Cell Lines and HUVECS RNA was extracted from human leukocyte cell lines and from HUVECS as described in Example 6, and was analyzed by northern blot hybridization (also as described in Example 6) by probing with either ICAM-R or ICAM-1 cDNA. After phosphorimaging of the initial hybridization, blots were stripped and reanalyzed using a human actin probe. The results of the actin normalized northerns of ICAM-R and ICAM-1 probed blots are presented in FIG. 5(A through B) as bar graphs. At the RNA level, ICAM-R was expressed in a variety of leukocytic cell types and its expression was not necessarily concomitant with the expression of ICAM-1 RNA. For example, unstimulated HUVECS express low levels of ICAM-1 and expression is upregulated following TNF stimulation (5B). In contrast, detectable levels of ICAM-R message were not observed in either case in HUVECS (5A).

EXAMPLE 9

Immunoprecipitations of detergent solubilized lysates of surface biotinylated human cell lines KG1a, K562 and CEM were performed using the four anti-ICAM-R monoclonal antibodies: 26H11C-2, 26E3D-1, 26I10E-2, and 26I8F-2.

Cell surface proteins on human leukocyte cell lines KG1, K562, and CEM were labelled by reaction with sulfo-NHS-biotin (Pierce Chemical Company, Rockford, Ill.) as follows. For each reaction $0.5-1\times10^7$ cells were washed twice in phosphate buffered saline (PBS), resuspended in 1 ml PBS and 10 µl of 100 mM sulfo-NHS-biotin diluted in PBS was added. Following incubation for 10 minutes at 37° C. the cells were washed once with PBS, and 4 ml of 10 mM Tris pH 8.4, 0.25M sucrose was added and the cells were then incubated for 30 minutes at 4° C. with gentle mixing. The cells were pelleted by centrifugation, the supernatant was aspirated and the pellet was solubilized with 300 µl of 10 mM Tris pH 8, 50 mM NaCl, 1% Triton X-100, 1 mM phenylmethylsulfonyl fluoride, 1 mM EDTA by incubating on ice for 15 minutes. The lysate was clarified by centrifugation and the supernatant was precleared by addition of 25 µl normal mouse serum and incubation for 1 hour at 4° C. This step was followed by the addition of 20 µl of a 50/50 (v/v) solution of protein-A sepharose beads (Sigma) that had been preincubated with 20 µg of affinity purified rabbit anti-mouse Immunoglobulin (Zymed). After incubation for 30 minutes at 4° C., the sepharose beads were removed by centrifugation.

Specific immunoprecipitations were then performed by addition of 20 µl of sepharose beads that had been prearmed by sequential incubation with rabbit anti-mouse immunoglobulin and either anti-ICAM-R or control monoclonal antibodies. Following overnight incubation at 4° C. with agitation, sepharose beads were pelleted in a microcentrifuge and washed sequentially 2× with 1 ml 10 mM Hepes ph 7.3, 150 mM NaCl, 1% Triton X-100; 1×with 0.1M Tris pH 8, 0.5M LiCl, 1% beta mercaptoethanol; and 1×with 20 mM Tris pH 7.5, 50 mM NaCl, 0.5% NP-40. Beads were then eluted with 50 µl 150 mM Tris pH 6.8, bromphenol blue, 20% beta mercaptoethanol, 4% SDS and 20% glycerol; boiled for 5 minutes; and pelleted by centrifugation. 35 µl of the resulting eluate was then analyzed by SDS-PAGE (10% acrylamide). After electrophoresis, proteins were electroblotted onto Immobilon-P membranes (Millipore, Bedford, Mass.) and incubated in 2% bovine serum albumin diluted in Tris buffered saline containing 0.2% Tween-20 for 20 minutes at 4° C. Blots were then incubated with horseradish peroxidase coupled to streptavidin (Vector Laboratories, Burlingame, Calif.) in TBS-Tween at room temperature for 20 minutes. Following 3 rinses in TBS-Tween, ECL western blotting detection reagents (Amersham) were added and chemiluminescent bands were visualized on Kodak X-OMAT-AR film.

Figure 6A:
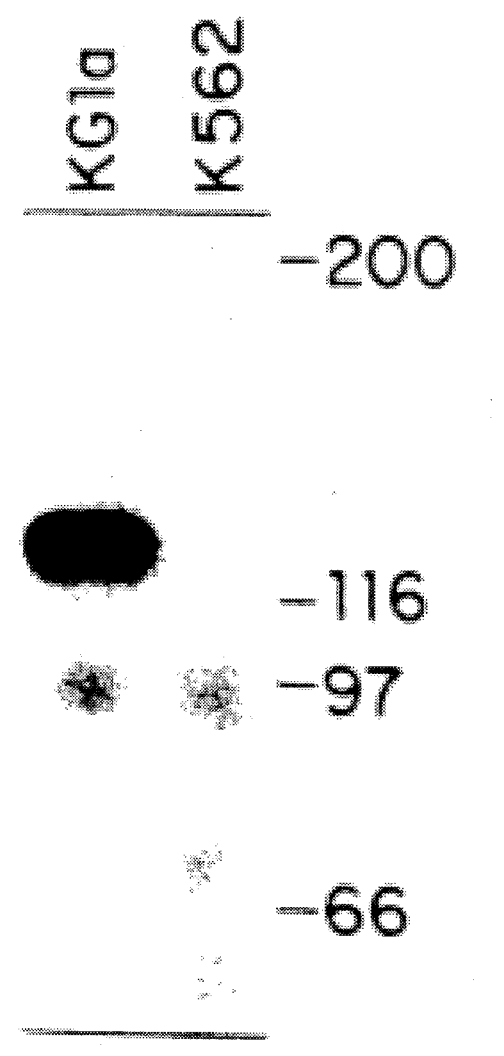
Figure 6B:
Figure 6B:
Figure 7A:
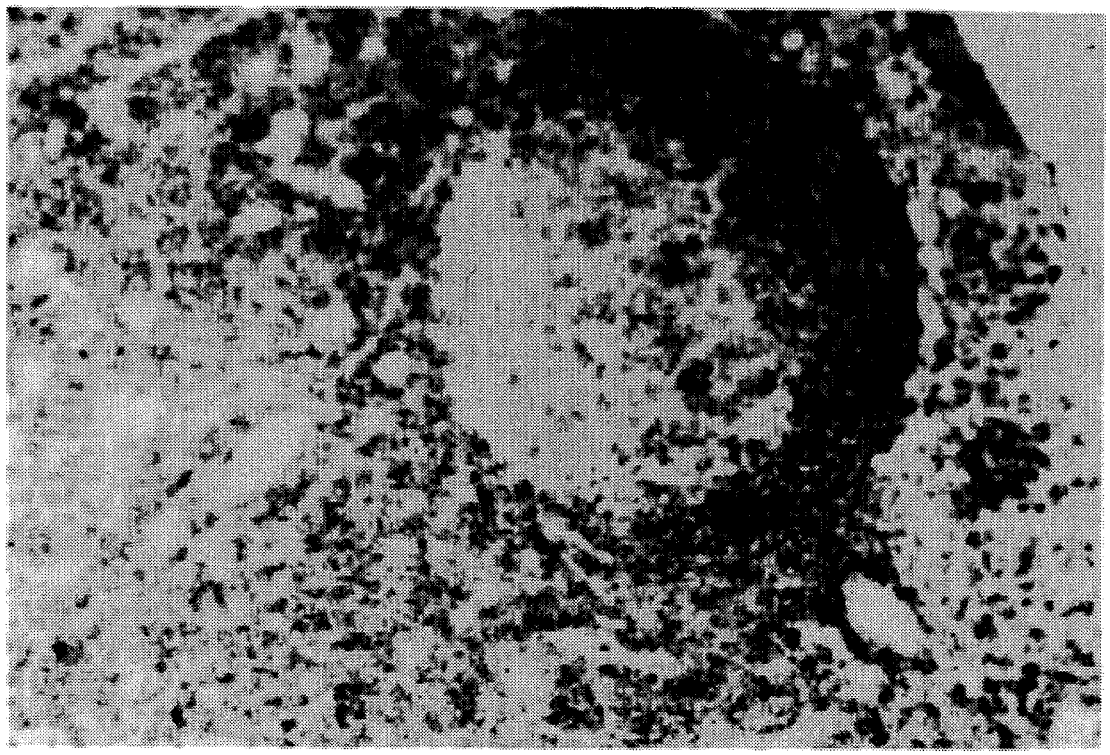
Figure 7B:
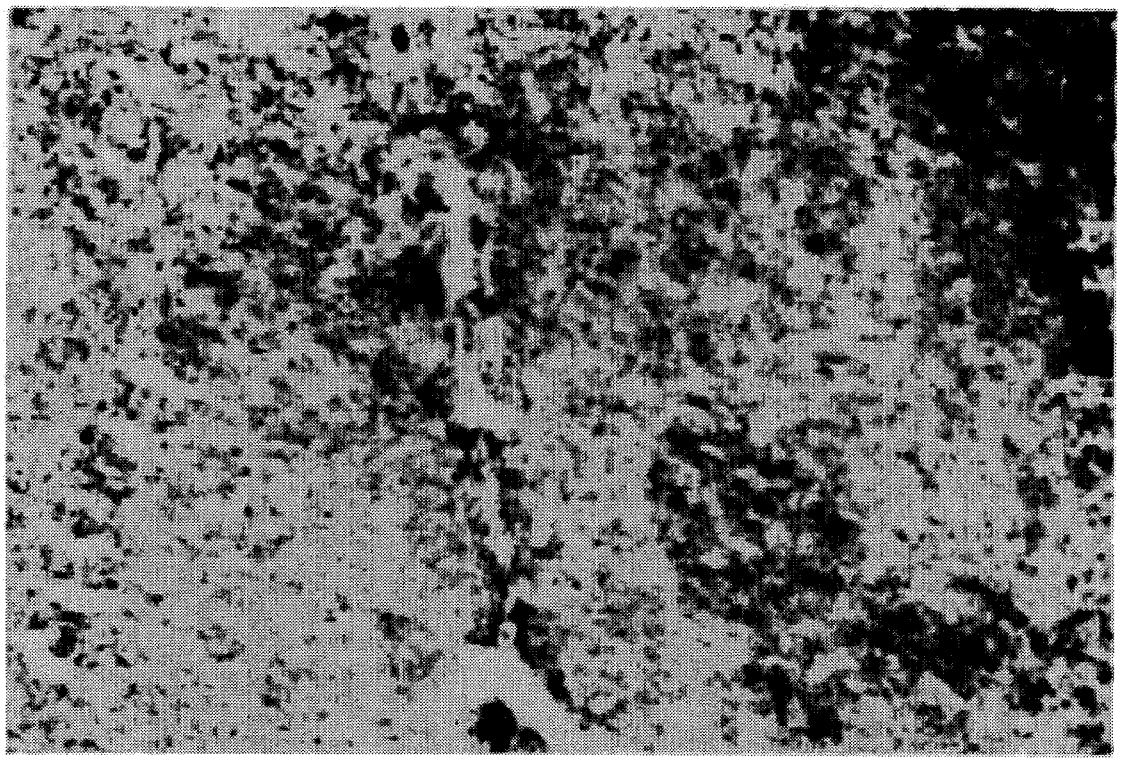
Figure 7C:
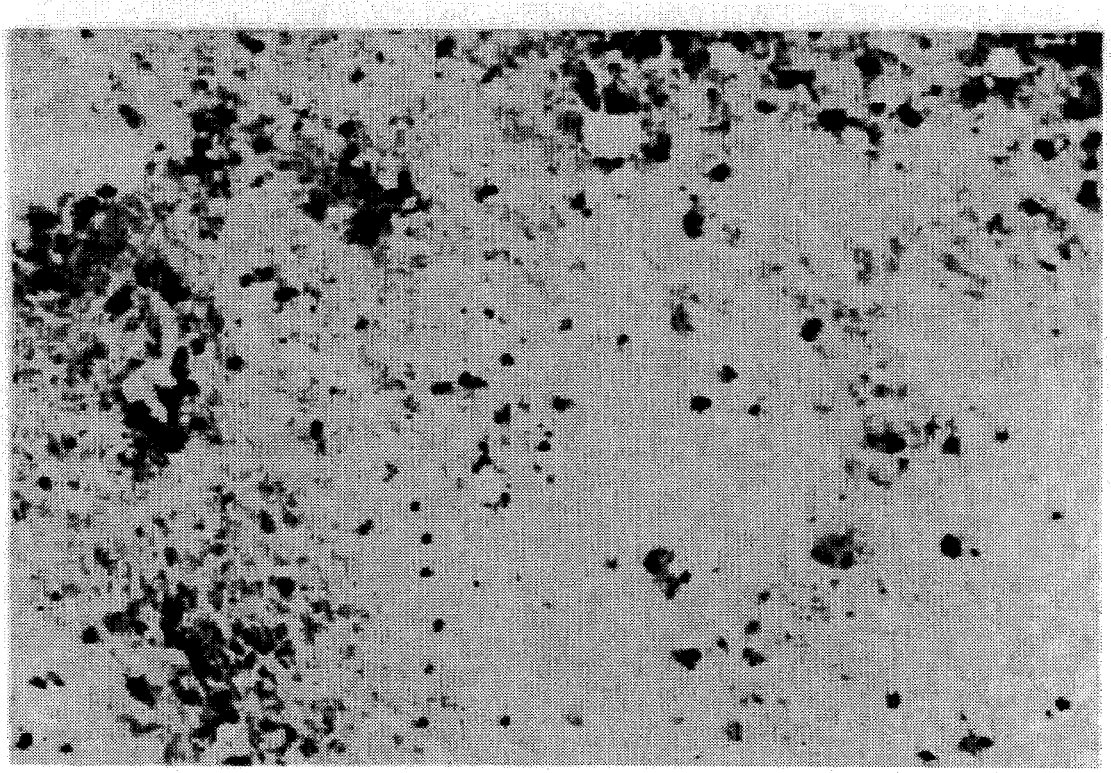
Figure 7D:
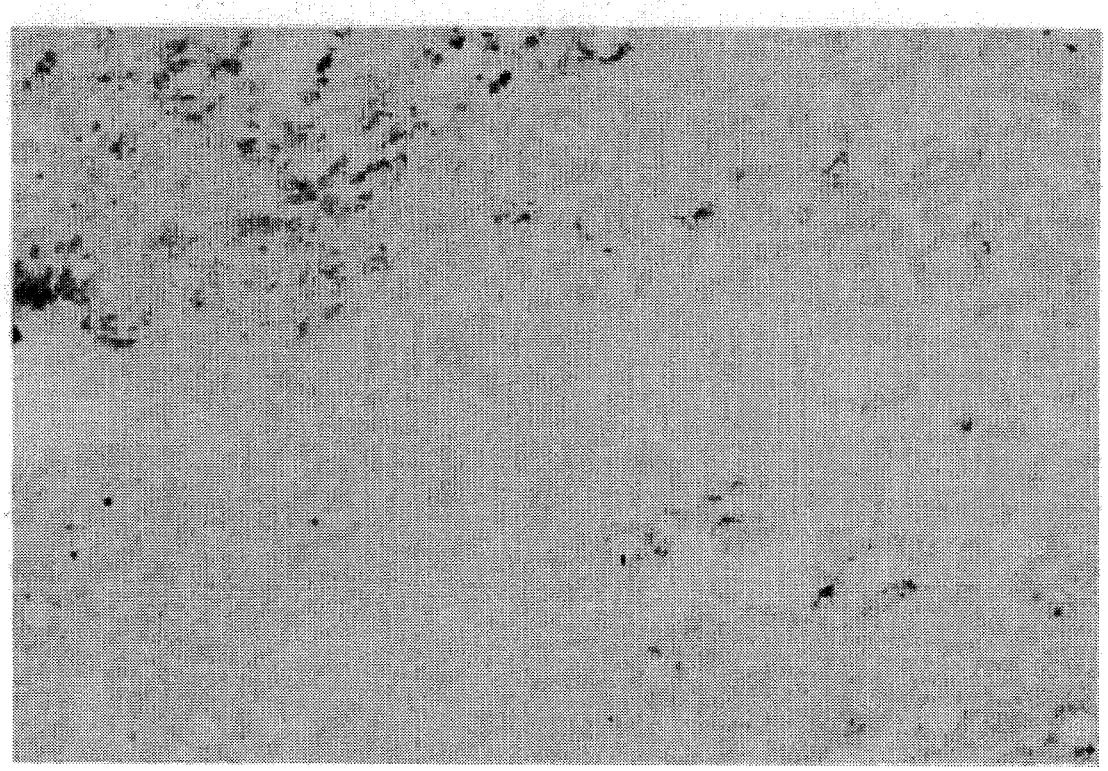
Figure 7E:
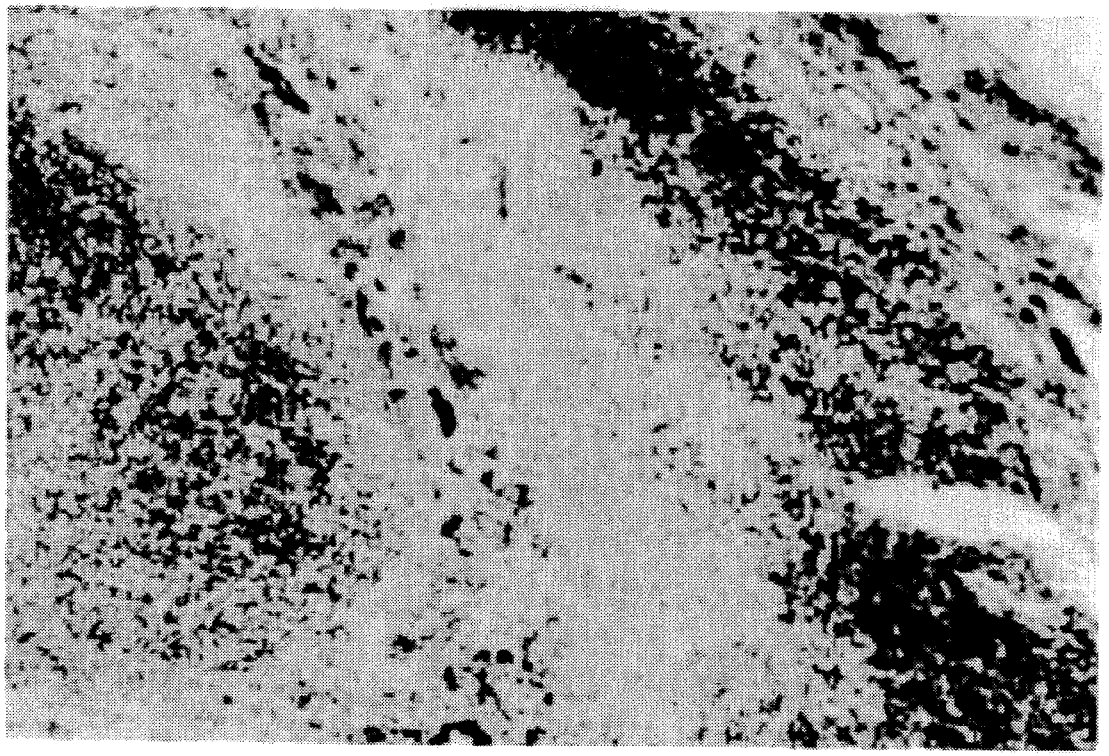
Figure 7F:
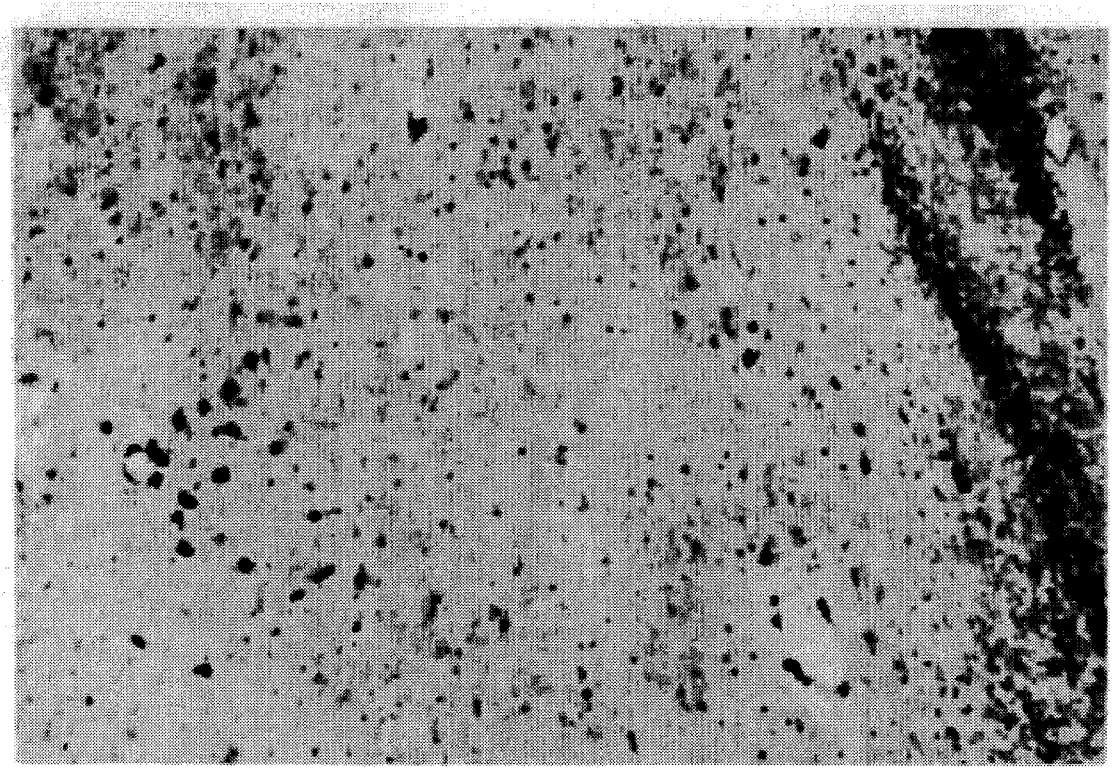
Figure 7G:
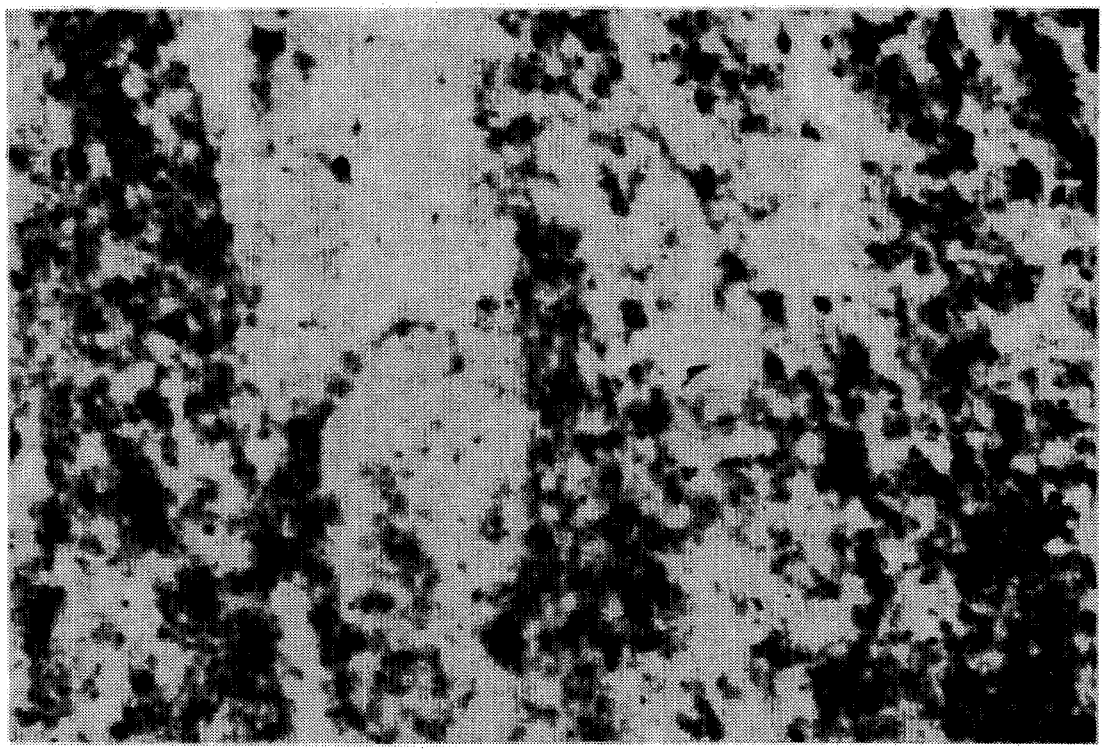

FIG. 6(A through B) shows the resulting western blots. A single specifically precipitated species of 120 kD was observed in immunoprecipitates with monoclonal antibody 26H11C-2 from KG1 cells, but not from K562 cells (See 6A).

A 120 kD band was also resolved in immunoprecipitates of the T cell line CEM (FIG. 6B, wherein Lane A was reacted with monoclonal antibody 26H 11 C-2; Lane B, monoclonal antibody 26I 10E-2; Lane C, monoclonal antibody 2618E; Lane D, monoclonal antibody 26E3D-1; and Lane E, a negative control antibody). The size of the ICAM-R species resolved in other immunoprecipitations varied slightly depending on the cellular source. Slightly larger forms of ICAM-R (~124 kD) were observed in cell lines such as the myeloid cell line, HL-60. Given the predicted size (about 52 kD) of the core peptide based on the nucleotide sequence of the ICAM-R gene, these results imply that ICAM-R is heavily modified post-translationally to yield the mature cell surface form of the protein.

EXAMPLE 10

Immunohistologic staining with anti-ICAM-R monoclonal antibody 26I10E-2 and control antibodies was carried out on various human tissues including tonsil, liver, and brain (both normal and multiple sclerosis-afflicted brain tissue).

Sections (6 μm) of various tissues were layered onto Vectabond coated slides and stored at −70° C. (some sections were stored at −20° C.). Prior to use, slides were removed from −70° C. and placed at 55° C. for 5 minutes. Sections were then fixed in cold acetone for 10 minutes and air dried. Sections were blocked in a solution containing 1% BSA, 60% normal human sera, and 6% normal horse sera for 30 minutes at room temperature. Primary antibody directed against ICAM-R (26I10E-2) diluted 1:50 or a negative control antibody or anti-ICAM-1 monoclonal antibody was applied to each section for 1 hour at room temperature. Unbound antibody was washed off by immersing the slides in 1× PBST for 5 minutes (repeated 3 times). Biotinylated anti-mouse immunoglobulin (Vector Laboratories) was then applied to each section in the same fashion. ABCHPO (Avidin-Biotin Complex-HPO) was used to detect the second antibody. A solution of reagent A (9 μl) (Vector Laboratories) combined with reagent B (9 μl) (Vector Laboratories) in 1 ml of 1% BSA/PBST was applied to each section for 30 minutes at room temperature. Slides were then washed in 1× PBST (repeated 3 times). DAB (3'3 Diaminobenzidine-Tetrahydrochloride, Sigma) substrate (stock: 600 mg/ml DAB diluted 1:10 in 0.05M Tris Buffer, pH 7.6, add 3% $H_2O_2$ to a final concentration of 1%) was applied to each slide for 8 minutes at room temperature. Slides were washed in water for 5–10 minutes at room temperature and 1% osmic acid (to enhance color development) was added for one minute at room temperature. Slides were then washed in tap water for 5–10 minutes and counterstained in 1% Nuclear Fast Red (NFR) for 30 seconds at room temperature. Slides were alcohol dehydrated, treated with Histroclear and mounted with coverslips using histomount.

The results of staining with the monoclonal antibodies are presented in FIG. 7(A through G) as photomicrographs wherein the tissue in 7A, 7B and 7E is human tonsil; in 7C and 7D is human liver; in 7F is brain from a human patient afflicted with multiple sclerosis; and in 7G is normal human brain. Sections shown in 7A, 7C, 7F and 7G were stained with anti-ICAM-R monoclonal antibody 26I10E-2. Sections shown in 7B and 7D were stained with the negative control antibody, while the section shown in 7E was stained with the anti-ICAM-1 antibody. Staining revealed high level expression of ICAM-R in lymphoid tissues such as tonsil (7A). Expression was also detected on tissue leukocytes in other nonlymphoid organs such as the liver wherein Kupfer cells (liver macrophages) were positively stained (7C). Evidence that ICAM-1 and ICAM-R expression are regulated distinctly in vivo is given by the staining pattern observed in tonsil and lymph node: ICAM-1 is strongly expressed on B cells in follicles and germinal centers whereas ICAM-R was not observed on activated B cells in the germinal centers (7A and 7E). Significantly, ICAM-R expression was also detected on leukocytes infiltrating sites of inflammation. For example, ICAM-R expression was observed on perivascular infiltrating leukocytes in the brain tissue of individuals afflicted with multiple sclerosis (7F). Similar staining was not observed in anatomically equivalent locations of brain tissue from normal individuals (7G).

EXAMPLE 11

In order to determine whether ICAM-R is involved in homotypic cell adhesion, aggregation assays were performed with a panel of cell lines including T lymphoblastoid cell lines (Sup T1, CEM, Molt 4, Hut 78, Jurkat, SKW3), B lymphoblastoid cells lines (Jijoye, Raji), monocytic cell lines (U937, HL60), a myelogenous cell line (KG-1) and an erythroleukemia cell line (K562). To determine the function of the ICAM-R molecule, the cells were incubated with various antibodies before aggregation was assayed. Anti-ICAM-R supernatants produced by hybridomas 26H11C-2, 26E3D-1, 26I10E-2, and 26I8F-2 were used as well as antibody preparations known to block aggregation through a β2 integrin pathway: TS1/18 (ATCC Accession #HB203) specific for the CD18 molecule, the β subunit of LFA-1; TS1/22 (ATCC Accession #HB202) specific for the CD11a molecule, the α-chain of LFA-1; and LM2/1 (ATCC Accession #HB204) specific for the CD11b molecule, the α subunit of MAC-1. Purified anti-ICAM-1 antibody and hybridoma supernatant directed against the α-chain of the VLA-4 molecule (clone 163H) were used as controls.

Aggregation assays were done in duplicate, with and without addition of phorbol 12-myristate 13-acetate (PMA) (50 ng/ml). $3 \times 10^5$ cells in RPMI 1640 medium with 10% fetal calf serum were added in a flat-bottomed 96-well microtest plate. When one antibody was tested in an experiment, 50 μl of purified antibody or hybridoma supernatant were added to the wells (PMA was added at the same time to selected wells). When two antibodies were tested in the same experiment, the antibodies were incubated sequentially at room temperature for 30 minutes each and then the cells were incubated at 37° C. for 10 minutes. Incubating the antibodies before addition of PMA or at the same time as the PMA did not cause any significant change in the aggregation results. After incubation with the antibody or antibodies, cells were uniformly resuspended and then incubated at 37° C. for 4 to 24 hours. Aggregation scoring was done with an inverted microscope. In each experiment, the efficacy of the PMA stimulation was checked in parallel by stimulating Raji cells with an equal amount of PMA and determining the amount of aggregation blockable by monoclonal antibodies to CD18, CD11a, and CD54 (ICAM-1) molecules.

Tables 2, below, sets out the results of one representative aggregation experiment wherein PMA was added. Aggregation scores are reported on a range from 0 to 5, wherein 0 indicated that no cells were in clusters; 1 indicated that less than 10% of the cells were in clusters; 2 indicated that 10 to 50% cells were aggregated; 3 indicated that 50 to 100% cells were in loose clusters; 4 indicated that almost 100% of the cells were in compact aggregates and 5 than 100% of the cells were in very large and compact cell aggregates.

TABLE 2

| Antibody Treatment | | | | | | | | | |
|---|---|---|---|---|---|---|---|---|---|
| Antibody 1 | — | — | — | — | — | — | αCD18 | αCD11a | αCD11b |
| Antibody 2 | — | αCD18 | αCD11a | αCD11b | 26H11C | 26I10E | 26H11C | 26H11C | 26H11C |
| Aggregation | | | | | | | | | |
| SUPT1 cells (after 4 hours) | 2 | 1 | 1 | 2 | 4 | 2 | 2 | 2 | 4 |
| SUPT1 cells (after 24 hours) | 2 | 1 | 1 | 2 | 4 | 2 | 2 | 2 | 4 |

Interestingly, treatment with three of the antibodies specific for ICAM-R (26H11C-2, 26E3D-1 and 26I8F-2) stimulated homotypic cell-cell aggregation (data for 26E3D-1 and 26I8F-2 not shown). Stimulation occurred in both the presence and absence of co-stimulatory agents such as a phorbol ester (PMA). The fourth anti-ICAM-R monoclonal antibody (26I10E-2) had no effect on cell aggregation. At least a portion of the aggregation stimulated by anti-ICAM-R antibodies in PMA treated cells was blocked by pretreatment with monoclonal antibodies against CD18 or CD11a indicating that one or more leukointegrins may participate in this type of adhesion.

Preliminary experiments testing the adhesion of leukocytes to transfected L cells expressing ICAM-R on their surface indicate that ICAM-R may be a ligand/receptor for an adhesion molecule or molecules on leukocytes.

The foregoing illustrative examples relate to presently preferred embodiments of the invention and numerous modifications and variations thereof will be expected to occur to those skilled in the art.

Clearly, polynucleotides (e.g., DNA and RNA) encoding ICAM-R are useful not only in securing expression of ICAM-R and variant polypeptides; they may readily be employed to identify cells (especially cells involved in inflammatory processes) which express ICAM-R in a normal or activated state. Typical detection assays involving ICAM-R DNA include Northern blot hybridization, RNAse protection, and in situ hybridization cytological assays wherein the DNA or RNA (in suitably labelled, detectable form) hybridizes to RNA in the sample. ICAM-R encoding DNA (especially DNA encoding the first, fourth and fifth domains which have less homology to DNAs encoding ICAM-1 and ICAM-2 than the DNAs encoding domains 2 and 3) is expected to be useful in isolating genomic DNA encoding ICAM-R including genomic DNA specifying endogenous expression control DNA sequences for ICAM-R DNA. As previously noted, knowledge of polynucleotide sequences encoding ICAM-R and/or controlling expression of ICAM-R makes available a variety of antisense polynucleotides useful in regulating expression of ICAM-R.

The present invention makes available the production of ICAM-R polypeptides and variants thereof, especially including water soluble fragments thereof, such as fragments comprising one or more of the five immunoglobulin-like domains of ICAM-R in glycosylated, non-glycosylated, or de-glycosylated forms. Pharmaceutical compositions including the protein products of the invention have therapeutic potential in the treatment of inflammatory disease processes, e.g., as competitive inhibitors or stimulatory agents of ligand/receptor binding reactions involving ICAM-R. Such therapeutic potential is especially projected for "immunoadhesin" type recombinant hybrid fusion proteins containing, at their amino terminal, one or more domains of ICAM-R and, at their carboxy terminal, at least one constant domain of an immunoglobulin. Such hybrid fusion proteins are likely to be available in the form of homodimers wherein the Ig portion provides for longer serum half life and the ICAM-R portion has greater affinity for the ICAM-R binding partner than ICAM-R itself. Other multimeric forms of ICAM-R which may have enhanced avidity are also projected to have therapeutic potential.

Antibody substances and binding proteins, especially monospecific antibodies including monoclonal and polyclonal antibodies, are made readily available by the present invention through the use of immunogens comprising cells naturally expressing ICAM-R, recombinant host cells producing polypeptide products of the invention, the ICAM-R polypeptide products themselves, and polypeptide products of the invention bound to an ICAM-R specific antibody that stimulates cell-cell aggregation (i.e., polypeptide products that may be in a "high affinity" binding conformation). Such antibodies and other ICAM-R specific binding proteins can be employed for immunopurification of ICAM-R and variants and in pharmaceutical compositions for therapies premised on blocking and/or stimulating the ligand/receptor binding of ICAM-R and soluble fragments thereof. For use in pharmaceutical compositions, ICAM-R specific antibody and anti-idiotypic antibody substances may be humanized (e.g., CDR-grafted) by recombinant techniques well-known in the art. Antibodies specific for distinct regions of ICAM-R may be employed in ELISA systems involving immunological "sandwiches" for monitoring inflammatory processes characterized by increases in amounts of soluble ICAM-R polypeptides in body fluids such as serum.

Inflammatory conditions which may be treated or monitored with ICAM-R related products include conditions resulting from a response of the nonspecific immune system in a mammal (e.g., adult respiratory distress syndrome, multiple organ injury syndrome secondary to septicemia, multiple organ injury syndrome secondary to trauma, reperfusion injury of tissue, acute glomerulonephritis, reactive arthritis, dermatosis with acute inflammatory components, stroke, thermal injury, hemodialysis, leukapheresis, ulcerative colitis, Crohn's disease, necrotizing enterocolitis, granulocyte transfusion associated syndrome, and cytokine-induced toxicity) and conditions resulting from a response of the specific immune system in a mammal (e.g., psoriasis, organ/tissue transplant rejection and autoimmune diseases including Raynaud's syndrome, autoimmune thyroiditis, EAE, multiple sclerosis, rheumatoid arthritis and lupus erythematosus). ICAM-R products of the invention may also be useful in monitoring and treating asthma, tumor growth and/or metastasis, and viral infection (e.g., HIV infection).

Thus only such limitations as appear in the appended claims should be placed upon the scope of the present invention.

What is claimed is:

1. A method for detecting a cell expressing ICAM-R comprising hybridizing a detectably labeled polynucleotide with mRNA of said cell and detecting hybridization by detecting the presence of said labeled polynucleotide, wherein said labeled polynucleotide encodes the ICAM-R polypeptide set out in SEQ ID NO: 1 or encodes an ICAM-R specific polypeptide fragment of SEQ ID NO: 1.

\* \* \* \* \*

UNITED STATES PATENT AND TRADEMARK OFFICE
CERTIFICATE OF CORRECTION

PATENT NO. : 5,532,127

DATED : July 2, 1996

INVENTORS : GALLATIN ET AL.

It is certified that error appears in the above-identified patent and that said Letters Patent is hereby corrected as shown below:

Title page,
Item [54], Title, replace "ASSAY FOR 1-CAM RELATED PROTEIN EXPRESSION" with --METHOD FOR DETECTING CELLS EXPRESSING ICAM-R--;

Column 6, line 25, replace "*Ann. Rev,*" with --*Ann. Rev.*--;

Column 6, line 26, replace "et at.," with --et al.--;

Column 8, line 37, replace "X-gat" with --X-gal--;

Column 10, line 35, replace "CCGGTYCTTGGAGGTGGAA" with
--CCGGTTCTTGGAGGTGGAA--;

Column 10, line 37, replace "CATGACTGTCGCATICAGCA" with
--CATGACTGTCGCATTCAGCA--;

Column 10, lines 40 replace "GCAAGAACCTYACCCTAC;" with
--GCAAGAACCTTACCCTAC--.

Column 11, line 67, replace "49 matches" with --249 matches--.

Column 12, line 26, replace "bases 4 18" with --bases 418--.

Column 12, line 35, replace "Example 4." with --Example 4).--.

Column 14, line 25, replace "NaCl 20" with --NaCl, 20--.

UNITED STATES PATENT AND TRADEMARK OFFICE
CERTIFICATE OF CORRECTION

PATENT NO. : 5,532,127

DATED : July 2, 1996

INVENTORS : GALLATIN ET AL.

It is certified that error appears in the above-identified patent and that said Letters Patent is hereby corrected as shown below:

Column 15, line 59, replace "NAN$_3$)," with --NaN$_3$),--.

Column 16, lines 4-5, replace "supenatant were" with --supernatants were--.

Column 16, line 6, replace "F(ab')" with --F(ab')2--.

Column 16, line 17, replace "Supenatant from" with --Supernatants from--.

Column 16, line 20, replace "2618F-2," with --26I8F-2,--.

Column 16, line 47, replace "aliamine" with --diamine--.

Column 17, line 18, replace "Blymphocytes," with --B lymphocytes,--.

Column 17, line 36, replace "B Cell, JUOYE..." with --B Cell, JIJOYE...--.

Column 17, line 52, replace "onHuman" with --on Human--;

Column 17, line 56 replace "antioICAM-R" with --anti-ICAM-R--.

Column 17, line 61, replace "monitoromg" with --monitoring--.

Column 18, line 51, replace "Hepes ph" with --Hepes pH--.

Column 19, line 10, replace "26I I0E-2:" with --26H11C-2; --.

UNITED STATES PATENT AND TRADEMARK OFFICE
CERTIFICATE OF CORRECTION

PATENT NO. : 5,532,127
DATED : July 2, 1996
INVENTORS : GALLATIN ET AL.

It is certified that error appears in the above-identified patent and that said Letters Patent is hereby corrected as shown below:

Column 19, line 11, replace "26I 10E-2;" with --26I10E-2;--.

Column 19, line 45, replace "ABCHPO" with --ABC-HPO--.

Column 21, line 6, replace "5 than" with --5 that--.

Signed and Sealed this

Twentieth Day of February, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 547 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 30..547

( x i ) SEQUENCE DESCRIPTION: SEQ ID NO:1:

```
Met  Ala  Thr  Met  Val  Pro  Ser  Val  Leu  Trp  Pro  Arg  Ala  Cys  Trp  Thr
               -25                      -20                           -15

Leu  Leu  Val  Cys  Cys  Leu  Leu  Thr  Pro  Gly  Val  Gln  Gly  Gln  Glu  Phe
               -10                      -5                             1

Leu  Leu  Arg  Val  Glu  Pro  Gln  Asn  Pro  Val  Leu  Ser  Ala  Gly  Gly  Ser
     5                          10                       15

Leu  Phe  Val  Asn  Cys  Ser  Thr  Asp  Cys  Pro  Ser  Ser  Glu  Lys  Ile  Ala
20                       25                      30                            35

Leu  Glu  Thr  Ser  Leu  Ser  Lys  Glu  Leu  Val  Ala  Ser  Gly  Met  Gly  Trp
               40                       45                            50

Ala  Ala  Phe  Asn  Leu  Ser  Asn  Val  Thr  Gly  Asn  Ser  Arg  Ile  Leu  Cys
               55                       60                            65

Ser  Val  Tyr  Cys  Asn  Gly  Ser  Gln  Ile  Thr  Gly  Ser  Ser  Asn  Ile  Thr
          70                       75                      80

Val  Tyr  Gly  Leu  Pro  Glu  Arg  Val  Glu  Leu  Ala  Pro  Leu  Pro  Pro  Trp
     85                       90                      95

Gln  Pro  Val  Gly  Gln  Asn  Phe  Thr  Leu  Arg  Cys  Gln  Val  Glu  Gly  Gly
100                      105                     110                          115

Ser  Pro  Arg  Thr  Ser  Leu  Thr  Val  Val  Leu  Leu  Arg  Trp  Glu  Glu  Glu
               120                     125                           130

Leu  Ser  Arg  Gln  Pro  Ala  Val  Glu  Glu  Pro  Ala  Glu  Val  Thr  Ala  Thr
               135                     140                           145

Val  Leu  Ala  Ser  Arg  Asp  Asp  His  Gly  Ala  Pro  Phe  Ser  Cys  Arg  Thr
          150                     155                     160

Glu  Leu  Asp  Met  Gln  Pro  Gln  Gly  Leu  Gly  Leu  Phe  Val  Asn  Thr  Ser
     165                     170                     175

Ala  Pro  Arg  Gln  Leu  Arg  Thr  Phe  Val  Leu  Pro  Val  Thr  Pro  Pro  Arg
180                      185                     190                          195

Leu  Val  Ala  Pro  Arg  Phe  Leu  Glu  Val  Glu  Thr  Ser  Trp  Pro  Val  Asp
               200                     205                           210

Cys  Thr  Leu  Asp  Gly  Leu  Phe  Pro  Ala  Ser  Glu  Ala  Gln  Val  Tyr  Leu
               215                     220                           225

Ala  Leu  Gly  Asp  Gln  Met  Leu  Asn  Ala  Thr  Val  Met  Asn  His  Gly  Asp
               230                     235                     240

Thr  Leu  Thr  Ala  Thr  Ala  Thr  Ala  Thr  Ala  Arg  Ala  Asp  Gln  Glu  Gly
     245                     250                     255
```

| | | | | | | | | | | | | | | |
|---|---|---|---|---|---|---|---|---|---|---|---|---|---|---|
| Ala | Arg | Glu | Ile | Val | Cys | Asn | Val | Thr | Leu | Gly | Gly | Glu | Arg | Arg | Glu |
| 260 | | | | | 265 | | | | 270 | | | | | 275 |
| Ala | Arg | Glu | Asn | Leu | Thr | Val | Phe | Ser | Phe | Leu | Gly | Pro | Ile | Val | Asn |
| | | | | 280 | | | | 285 | | | | | 290 | | |
| Leu | Ser | Glu | Pro | Thr | Ala | His | Glu | Gly | Ser | Thr | Val | Thr | Val | Ser | Cys |
| | | | 295 | | | | | 300 | | | | | 305 | | |
| Met | Ala | Gly | Ala | Arg | Val | Gln | Val | Thr | Leu | Asp | Gly | Val | Pro | Ala | Ala |
| | | 310 | | | | | 315 | | | | | 320 | | | |
| Ala | Pro | Gly | Gln | Thr | Ala | Gln | Leu | Gln | Leu | Asn | Ala | Thr | Glu | Ser | Asp |
| | 325 | | | | | 330 | | | | | 335 | | | | |
| Asp | Gly | Arg | Ser | Phe | Phe | Cys | Ser | Ala | Thr | Leu | Glu | Val | Asp | Gly | Glu |
| 340 | | | | | 345 | | | | | 350 | | | | | 355 |
| Phe | Leu | His | Arg | Asn | Ser | Ser | Val | Gln | Leu | Arg | Val | Leu | Tyr | Gly | Pro |
| | | | | 360 | | | | | 365 | | | | | 370 | |
| Lys | Ile | Asp | Arg | Ala | Thr | Cys | Pro | Gln | His | Leu | Lys | Trp | Lys | Asp | Lys |
| | | | 375 | | | | | 380 | | | | | 385 | | |
| Thr | Arg | His | Val | Leu | Gln | Cys | Gln | Ala | Arg | Gly | Asn | Pro | Tyr | Pro | Glu |
| | | 390 | | | | | 395 | | | | | 400 | | | |
| Leu | Arg | Cys | Leu | Lys | Glu | Gly | Ser | Ser | Arg | Glu | Val | Pro | Val | Gly | Ile |
| | 405 | | | | | 410 | | | | | 415 | | | | |
| Pro | Phe | Phe | Val | Asn | Val | Thr | His | Asn | Gly | Thr | Tyr | Gln | Cys | Gln | Ala |
| 420 | | | | | 425 | | | | | 430 | | | | | 435 |
| Ser | Ser | Ser | Arg | Gly | Lys | Tyr | Thr | Leu | Val | Val | Val | Met | Asp | Ile | Glu |
| | | | | 440 | | | | | 445 | | | | | 450 | |
| Ala | Phe | Ser | Ser | His | Phe | Val | Pro | Val | Phe | Ala | Val | Leu | Leu | Thr |
| | | | 455 | | | | 460 | | | | | 465 | | | |
| Leu | Gly | Val | Val | Thr | Ile | Val | Leu | Ala | Leu | Met | Tyr | Val | Phe | Arg | Glu |
| | | 470 | | | | | 475 | | | | | 480 | | | |
| His | Gln | Arg | Ser | Gly | Ser | Tyr | His | Val | Arg | Glu | Glu | Ser | Thr | Tyr | Leu |
| | 485 | | | | | 490 | | | | | 495 | | | | |
| Pro | Leu | Thr | Ser | Met | Gln | Pro | Thr | Glu | Ala | Met | Gly | Glu | Glu | Pro | Ser |
| 500 | | | | | 505 | | | | | 510 | | | | | 515 |
| Arg | Ala | Glu | | | | | | | | | | | | | |

(2) INFORMATION FOR SEQ ID NO:2:

( i ) SEQUENCE CHARACTERISTICS:
        ( A ) LENGTH: 1781 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CAGCTCTCTG TCAGAATGGC CACCATGGTA CCATCCGTGT TGTGGCCCAG GGCCTGCTGG      60
ACTCTGCTGG TCTGCTGTCT GCTGACCCCA GGTGTCCAGG GGCAGGAGTT CCTTTTGCGG     120
GTGGAGCCCC AGAACCCTGT GCTCTCTGCT GGAGGGTCCC TGTTTGTGAA CTGCAGTACT     180
GATTGTCCCA GCTCTGAGAA AATCGCCTTG GAGACGTCCC TATCAAAGGA GCTGGTGGCC     240
AGTGGCATGG GCTGGGCAGC CTTCAATCTC AGCAACGTGA CTGGCAACAG TCGGATCCTC     300
TGCTCAGTGT ACTGCAATGG CTCCCAGATA ACAGGCTCCT CTAACATCAC CGTGTACGGG     360
CTCCCGGAGC GTGTGGAGCT GGCACCCCTG CCTCCTTGGC AGCCGGTGGG CCAGAACTTC     420
ACCCTGCGCT GCCAAGTGGA GGGTGGGTCG CCCCGGACCA GCCTCACGGT GGTGCTGCTT     480
```

| | | | | | |
|---|---|---|---|---|---|
| CGCTGGGAGG | AGGAGCTGAG | CCGGCAGCCC | GCAGTGGAGG | AGCCAGCGGA | GGTCACTGCC | 540 |
| ACTGTGCTGG | CCAGCAGAGA | CGACCACGGA | GCCCCTTTCT | CATGCCGCAC | AGAACTGGAC | 600 |
| ATGCAGCCCC | AGGGGCTGGG | ACTGTTCGTG | AACACCTCAG | CCCCCCGCCA | GCTCCGAACC | 660 |
| TTTGTCCTGC | CCGTGACCCC | CCCGCGCCTC | GTGGCCCCCC | GGTTCTTGGA | GGTGGAAACG | 720 |
| TCGTGGCCGG | TGGACTGCAC | CCTAGACGGG | CTTTTTCCAG | CCTCAGAGGC | CCAGGTCTAC | 780 |
| CTGGCGCTGG | GGGACCAGAT | GCTGAATGCG | ACAGTCATGA | ACCACGGGGA | CACGCTAACG | 840 |
| GCCACAGCCA | CAGCCACGGC | GCGCGCGGAT | CAGGAGGGTG | CCCGGGAGAT | CGTCTGCAAC | 900 |
| GTGACCCTAG | GGGGCGAGAG | ACGGGAGGCC | CGGGAGAACT | TGACGGTCTT | TAGCTTCCTA | 960 |
| GGACCCATTG | TGAACCTCAG | CGAGCCCACC | GCCCATGAGG | GGTCCACAGT | GACCGTGAGT | 1020 |
| TGCATGGCTG | GGGCTCGAGT | CCAGGTCACG | CTGGACGGAG | TTCCGGCCGC | GGCCCCGGGG | 1080 |
| CAGACAGCTC | AACTTCAGCT | AAATGCTACC | GAGAGTGACG | ACGGACGCAG | CTTCTTCTGC | 1140 |
| AGTGCCACTC | TCGAGGTGGA | CGGCGAGTTC | TTGCACAGGA | ACAGTAGCGT | CCAGCTGCGA | 1200 |
| GTCCTGTATG | GTCCCAAAAT | TGACCGAGCC | ACATGCCCCC | AGCACTTGAA | ATGGAAAGAT | 1260 |
| AAAACGAGAC | ACGTCCTGCA | GTGCCAAGCC | AGGGGCAACC | CGTACCCCGA | GCTGCGGTGT | 1320 |
| TTGAAGGAAG | GCTCCAGCCG | GGAGGTGCCG | GTGGGGATCC | CGTTCTTCGT | CAACGTAACA | 1380 |
| CATAATGGTA | CTTATCAGTG | CCAAGCGTCC | AGCTCACGAG | GCAAATACAC | CCTGGTCGTG | 1440 |
| GTGATGGACA | TTGAGGCTGG | GAGCTCCCAC | TTTGTCCCCG | TCTTCGTGGC | GGTGTTACTG | 1500 |
| ACCCTGGGCG | TGGTGACTAT | CGTACTGGCC | TTAATGTACG | TCTTCAGGGA | GCACCAACGG | 1560 |
| AGCGGCAGTT | ACCATGTTAG | GGAGGAGAGC | ACCTATCTGC | CCCTCACGTC | TATGCAGCCG | 1620 |
| ACAGAAGCAA | TGGGGGAAGA | ACCGTCCAGA | GCTGAGTGAC | GCTGGGATCC | GGGATCAAAG | 1680 |
| TTGGCGGGGG | CTTGGCTGTG | CCCTCAGATT | CCGCACCAAT | AAAGCCTTCA | AACTCCCAAA | 1740 |
| AAAAAAAAAA | AAAAAAAAA | AAAAAAAAA | AAAAAAAAA | A | | 1781 |

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="The amino acid at this
            position can be a valine, a leucine or an
            isoleucine."

( i x ) FEATURE:
        ( A ) NAME/KEY: Modified-site
        ( B ) LOCATION: 6
        ( D ) OTHER INFORMATION: /note="The amino acid at this
            position can be a valine, a leucine or an
            isoleucine."

( x i ) SEQUENCE DESCRIPTION: SEQ ID NO:3:

Gly  Xaa  Xaa  Xaa  Xaa  Xaa  Xaa  Cys
  1                        5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 9
    ( D ) OTHER INFORMATION: /note="The amino acid at this position can be a valine or an alanine."

( x i ) SEQUENCE DESCRIPTION: SEQ ID NO:4:

Asp Xaa Gly Xaa Tyr Xaa Cys Xaa Xaa
1               5

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note="The amino acid at this position can be an asparagine or a serine."

( i x ) FEATURE:
    ( A ) NAME/KEY: Modified-site
    ( B ) LOCATION: 4
    ( D ) OTHER INFORMATION: /note="The amino acid at this position can be a lysine or a phenylalanine."

( i x ) FEATURE:
    ( A ) NAME/KEY: Modified-site
    ( B ) LOCATION: 6
    ( D ) OTHER INFORMATION: /note="The amino acid at this position can be an lysine or an isoleucine."

( i x ) FEATURE:
    ( A ) NAME/KEY: Modified-site
    ( B ) LOCATION: 7
    ( D ) OTHER INFORMATION: /note="The amino acid at this position can be an arginine or a glutamic acid."

( x i ) SEQUENCE DESCRIPTION: SEQ ID NO:5:

Gly Lys Xaa Xaa Thr Xaa Xaa Cys
1               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="The amino acid at this position can be a aspartic acid or a glutamic acid."

( i x ) FEATURE:
    ( A ) NAME/KEY: Modified-site
    ( B ) LOCATION: 2
    ( D ) OTHER INFORMATION: /note="The amino acid at this position can be a histidine or an aspartic acid."

( i x ) FEATURE:
    ( A ) NAME/KEY: Modified-site
    ( B ) LOCATION: 3
    ( D ) OTHER INFORMATION: /note="The amino acid at this position can be a histidine or a glycine."

(ix) FEATURE:
 (A) NAME/KEY: Modified-site
 (B) LOCATION: 4
 (D) OTHER INFORMATION: /note="The amino acid at this
  position can be a glycine or a histidine."

(ix) FEATURE:
 (A) NAME/KEY: Modified-site
 (B) LOCATION: 5
 (D) OTHER INFORMATION: /note="The amino acid at this
  position can be an alanine or an arginine."

(xi) SEQUENCE DESCRIPTION: SEQ ID NO:6:

```
Xaa  Xaa  Xaa  Xaa  Xaa  Asn  Phe  Ser  Cys
1                  5
```

(2) INFORMATION FOR SEQ ID NO:7:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:7:

ATTCTGCAGG CAARAAYCTS ACHMTBMGST G             31

(2) INFORMATION FOR SEQ ID NO:8:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:8:

ATTCTGCAGG CAARAGYTTY ACHMTBGART G             31

(2) INFORMATION FOR SEQ ID NO:9:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:9:

ATTCTGCAGG CAARTCYTTY ACHMTBGART G             31

(2) INFORMATION FOR SEQ ID NO:10:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:10:

ATTTCTAGAR AARTTRGCSC CRTGRTSRTC              30

5,532,127

33

34

-continued ( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ATTTCTAGAR AARTTSCKRT GSCCRTSKTC                                         30

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GAGACTCTGC ACTATGAGAC CTTCG                                                   25

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

CAGGTGATTC TCATGCAGAG TCCAGG                                             26

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CCGACATGCT GGTAAGTGTG TCCAA                                                25

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GACCATGAGG TGCCAAG                                                             17

( 2 ) INFORMATION FOR SEQ ID NO:16:

( i ) SEQUENCE CHARACTERISTICS:
        ( A ) LENGTH: 17 base pairs
        ( B ) TYPE: nucleic acid

```
            ( C ) STRANDEDNESS: single
            ( D ) TOPOLOGY: linear ( i i ) MOLECULE TYPE: DNA ( x i ) SEQUENCE DESCRIPTION: SEQ ID NO:16:

ATGGTCGTCT CTGCTGG                                                          17

( 2 ) INFORMATION FOR SEQ ID NO:17:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:17:

TTCACCCTGC GCTGCCAA                                                         18

( 2 ) INFORMATION FOR SEQ ID NO:18:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:18:

AAAGGGGCTC CGTGGTCG                                                         18

( 2 ) INFORMATION FOR SEQ ID NO:19:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:19:

CCGGTTCTTG GAGGTGGAA                                                        19

( 2 ) INFORMATION FOR SEQ ID NO:20:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:20:

CATGACTGTC GCATTCAGCA                                                       20

( 2 ) INFORMATION FOR SEQ ID NO:21:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA
```

(x i) SEQUENCE DESCRIPTION: SEQ ID NO:21:

GCAAGAACCT TACCCTAC 18

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:22:

GAAATTGGCT CCATGGTGA 19